(12) United States Patent
Frischmuth et al.

(10) Patent No.: US 12,257,267 B2
(45) Date of Patent: Mar. 25, 2025

(54) CLICK-MODIFIED MRNA

(71) Applicant: BASECLICK GMBH, Neuried (DE)

(72) Inventors: Thomas Frischmuth, Frischmuth (DE); Sascha Serdjukow, Kiefersfelden (DE); Birgit Graf, Munich (DE); Stefano Croce, Munich (DE)

(73) Assignee: BASECLICK GMBH, Neuried (DE)

( * ) Notice: Subject to any disclaimer, the term of this patent is extended or adjusted under 35 U.S.C. 154(b) by 29 days.

(21) Appl. No.: 18/046,020

(22) Filed: Oct. 12, 2022

(65) Prior Publication Data

US 2023/0226094 A1 Jul. 20, 2023

Related U.S. Application Data

(63) Continuation of application No. 16/955,837, filed as application No. PCT/EP2018/085676 on Dec. 18, 2018, now abandoned.

(30) Foreign Application Priority Data

Dec. 21, 2017 (EP) .................................... 17209585
Feb. 20, 2018 (EP) .................................... 18157703
Oct. 25, 2018 (EP) .................................... 18202542

(51) Int. Cl.
*C07H 21/02* (2006.01)
*A61K 31/7115* (2006.01)
*C12N 15/85* (2006.01)

(52) U.S. Cl.
CPC .......... *A61K 31/7115* (2013.01); *C12N 15/85* (2013.01)

(58) Field of Classification Search
CPC ................................................ A61K 31/7115
See application file for complete search history.

(56) References Cited

U.S. PATENT DOCUMENTS

| | | | |
|---|---|---|---|
| 8,883,516 B2 | 11/2014 | Manetto et al. | |
| 2013/0102655 A1 | 4/2013 | Kore et al. | |
| 2015/0050354 A1 | 2/2015 | Bouchon et al. | |
| 2018/0311343 A1 | 11/2018 | Huang et al. | |

FOREIGN PATENT DOCUMENTS

| | | | |
|---|---|---|---|
| JP | 2017504322 A | 2/2017 | |
| WO | 2015107115 A1 | 7/2015 | |
| WO | 2015196130 A2 | 12/2015 | |
| WO | 2016107877 A1 | 7/2016 | |
| WO | 2017049275 A2 | 3/2017 | |
| WO | 2017164738 A1 | 9/2017 | |
| WO | 2017201332 A1 | 11/2017 | |

OTHER PUBLICATIONS

Ugur Sahin et al., "mRNA-based therapeutics—developing a new class of drugs", Nature Reviews Drug Discovery, 2014, vol. 13, No. 10, pp. 759-780.
Zohra et al., Effective Delivery With Enhanced Translational Activity Synergistically Accelerates mRNA-based Transfection, Biochemical and Biophysical Research Communications, Amsterdam, 2007 vol. 358, No. 1, pp. 373-378.
Malwina Strenkowska et al., "Towards mRNA with superior translational activity: synthesis and properties of ARCA tetraphosphates with single phosphorothioate modifications", New Journal of Chem., 2010, vol. 34, No. 5, pp. 993-1007.
Isabell Hellmuth et al., "Bioconjugation of Small Molecules to RNA Impedes Its Recognition by Toll-like Receptor 7", Frontiers in Immunology, vol. 8, Mar. 24, 2017.
Cindy Y Jao and Adrian Salic, "Exploring RNA transcription and turnover in vivo by using click chemistry", Proceedings of the National Academy of Sciences, National Academy of Sciences, US, vol. 105, No. 41, Oct. 14, 2008.
International Preliminary Report on Patentability issued in International Application No. PCT/EP2018/085676 dated Aug. 27, 2020; 10 pages.
Nainar et al.; "Temporal Labeling of Nascent RNA Using Photoclick Chemistry in Live Cells"; Journal of the American Chemical Society; dated 2017; 4 pages.
Rao et al.; "Posttranscriptional chemical functionalization of azide-modified oligoribonucleotides by bioorthogonal click and Staudinger reactions"; Chem. Commun., 2012, 48, 498-500; dated Sep. 13, 2011; 4 pages.
Pyka et al.; "Diels-Aider Cycioadditions on Synthetic RNA in Mammalian Cells"; Bioconjugate Chem. 2014; dated 2014; 32 pages.
Muttach et al.; "Chemo-enzymatic modification of eukaryotic mRNA"; Ora. Stornof. Chem. 2017, 15, 278; dated Oct. 3, 2016; 7 pages.
Holstein et al.; "Dual 5' Cap Labeling Based on Regioselective RNA Methyltransferases and Bioorthogonal Reactions"; Chem. Eur.J. 2017; dated 2017; 9 pages.
Yin et al.; "Structure-guided chemical modification of guide RNA enables potent non-viral in vivo genome editing"; Nat Rmtechnol. Dec. 2017; dated Apr. 16, 2018; 22 pages.
Maassen et al.; "5-Ethynyluridine: A Bio-orthogonal Uridine Variant for mRNA-Based Therapies and Vaccines"; ChemBioChem 2023, 24; dated Jan. 31, 2023; 7 pages.

*Primary Examiner* — Amy Rose Hudson
(74) *Attorney, Agent, or Firm* — Meunier Carlin & Curfman LLC

(57) ABSTRACT

The present invention relates to alkyne- and/or azide-modified mRNA, processes for producing such modified mRNA, cells which are transfected to include the modified mRNA, pharmaceutical compositions containing the modified mRNA or cells including the modified mRNA, and to uses of such mRNA, cells or pharmaceutical compositions in mRNA based therapeutic and/or prophylactic applications.

20 Claims, 17 Drawing Sheets

Specification includes a Sequence Listing.

Figure 6

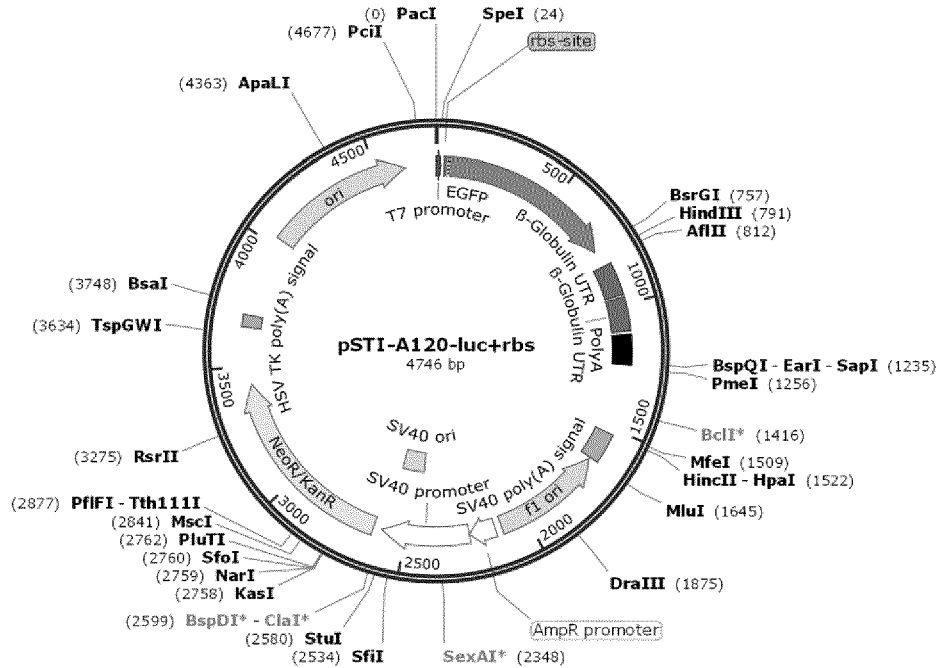

5'TAATACGACTCACTATAGGGCGAACTAGTAAGCAAGGAGGCGTGCAGATGGTGAG
CAAGGGCGAGGAGCTGTTCACCGGGGTGGTGCCCATCCTGGTCGAGCTGGACGGC
GACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGG
CCCACCCTCGTGACCACCCTGACCTACGGCGTGCAGTGCTTCAGCCGCTACCCCGA
CCACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGAAG
TTCGAGGGCGACACCCTGGTGAACCGCATCGAGCTGAAGGGCATCGACTTCAAGGA
GGACGGCAACATCCTGGGGCACAAGCTGGAGTACAACTACAACAGCCACAACGTCT
ATATCATGGCCGACAAGCAGAAGAACGGCATCAAGGTGAACTTCAAGATCCGCCACA
ACATCGAGGACGGCAGCGTGCAGCTCGCCGACCACTACCAGCAGAACACCCCCATC
GGCGACGGCCCCGTGCTGCTGCCCGACAACCACTACCTGAGCACCCAGTCCGCCC
TGAGCAAAGACCCCAACGAGAAGCGCGATCACATGGTCCTGCTGGAGTTCGTGACC
GCCGCCGGGATCACTCTCGGCATGGACGAGCTGTACAAGTCCGGCCGGACTCAGAT
CTCGAGCTCAAGCTTCGaattGATCCAGATCTTAAGTAAGTAAGCTCGAGAGCTCGCTT
TCTTGCTGTCCAATTTCTATTAAAGGTTCCTTTGTTCCCTAAGTCCAACTACTAAACTG
GGGGATATTATGAAGGGCCTTGAGCATCTGGATTCTGCCTAATAAAAAACATTTATTT
TCATTGCTGCGTCGAGAGCTCGCTTTCTTGCTGTCCAATTTCTATTAAAGGTTCCTTT
GTTCCCTAAGTCCAACTACTAAACTGGGGGATATTATGAAGGGCCTTGAGCATCTGG
ATTCTGCCTAATAAAAAACATTTATTTTCATTGCTGCGTCGAGAGCTAAAAAAAAAAAA
AAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAA 3'

Eterneon Red eGFP mRNA

SEQUENCE LISTING

```
Sequence total quantity: 2
SEQ ID NO: 1            moltype = RNA  length = 31
FEATURE                 Location/Qualifiers
misc_feature            1..31
                        note = RNA oligonucleotide
source                  1..31
                        mol_type = other RNA
                        organism = synthetic construct
SEQUENCE: 1
ctagtgcagt acatgtaatc gaccagatca a                                    31

SEQ ID NO: 2            moltype = DNA  length = 1239
FEATURE                 Location/Qualifiers
misc_feature            1..1239
                        note = partial sequence of pSTI-A120-luc+rbs (from T7
                         promoter topoly(A))
source                  1..1239
                        mol_type = other DNA
                        organism = synthetic construct
SEQUENCE: 2
taatacgact cactataggg cgaactagta agcaaggagg cgtgcagatg gtgagcaagg      60
gcgaggagct gttcaccggg gtggtgccca tcctggtcga gctggacggc gacgtaaacg     120
gccacaagtt cagcgtgtcc ggcgagggcg agggcgatgc cacctacggc aagctgaccc     180
tgaagttcat ctgcaccacc ggcaagctgc ccgtgccctg gcccaccctc gtgaccaccc     240
tgacctacgg cgtgcagtgc ttcagccgct accccgacca tatgaagcag cacgacttct     300
tcaagtccgc catgcccgaa ggctacgtcc aggagcgcac catcttcttc aaggacgacg     360
gcaactacaa gacccgcgcc gaggtgaagt tcgagggcga caccctggtg aaccgcatcg     420
agctgaaggg catcgacttc aaggaggacg gcaacatcct ggggcacaag ctggagtaca     480
actacaacag ccacaacgtc tatatcatgg ccgacaagca gaagaacggc atcaaggtga     540
acttcaagat ccgccacaac atcgaggacg gcagcgtgca gctcgccgac cactaccagc     600
agaacacccc catcggcgac ggccccgtgc tgctgcccga caaccactac ctgagcaccc     660
agtccgccct gagcaaagac cccaacgaga gcgcgatca catggtcctg ctggagttcg     720
tgaccgccgc cgggatcact ctcggcatgg acgagctgta caagtccggc cggactcaga     780
tctcgagctc aagcttcgaa ttgatccaga tcttaagtaa gtaagctcga gagctcgctt     840
tcttgctgtc caatttctat taaaggttcc tttgttccct aagtccaact actaaactgg     900
gggatattat gaagggcctt gagcatctgg attctgccta ataaaaaaca tttattttca     960
ttgctgcgtc gagagctcgc tttcttgctg tccaatttct attaaaggtt cctttgttcc    1020
ctaagtccaa ctactaaact gggggatatt atgaagggcc ttgagcatct ggattctgcc    1080
taataaaaaa catttatttt cattgctgcg tcgagagcta aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaa                            1239
```

CLICK-MODIFIED MRNA

INCORPORATION BY REFERENCE

The contents of the XML file named "10593-039US2SequenceListing.xml" which was created on Oct. 12, 2022, and is 4.7 KB in size, are hereby incorporate by reference in their entirety.

The present invention relates to alkyne- and/or azide-modified mRNA, processes for producing such modified mRNA, cells which are transfected to include the modified mRNA, pharmaceutical compositions containing the modified mRNA or cells including the modified mRNA, and to uses of such mRNA, cells or pharmaceutical compositions in mRNA based therapeutic and/or prophylactic applications. Finally, the invention relates to a method of stabilizing RNA by introducing alkyne- and/or azide-modified nucleotides and/or further to methods for determining delivery of modified mRNA into target cells and/or expression of a protein product encoded by the modified mRNA.

BACKGROUND OF THE INVENTION

Messenger RNA (mRNA) is the template molecule that is transcribed from cellular DNA and is translated into an amino acid sequence, i.e. a protein, at ribosomes in the cells of an organism. In order to control the expression level of the encoded proteins, mRNAs possess untranslated regions (UTRs) flanking the actual open reading frame (ORF) which contains the genetic information encoding the amino acid sequence. Such UTRs, termed the 5'-UTR and the 3'-UTR, respectively, are sections of the mRNA located before the start codon and after the stop codon. Further, mRNA contains a poly(A) tail region which is a long sequence of adenine nucleotides which promotes export of mRNA from the nucleus, translation and to some extent protects the mRNA from degradation.

Due to its chemical and biochemical properties, mRNA usually is degraded within a few minutes inside of cells, thus expression of a specific protein usually is a transient process. Moreover, the polyanionic mRNA molecule is not well suited to cross a cell membrane which renders external delivery of mRNA extremely difficult.

Despite these challenges associated with mRNA, scientific and technological advances of the recent years have made mRNA a promising candidate for a novel class of drugs. Sahin U. et al., *Nat. Publ. Gr.* 13, 759-780 (2014) provide an overview on mRNA-based therapeutics and drug development. mRNA is for example used to trigger in vivo production of proteins like antibodies and enzymes, or to stimulate an immune response, e.g. by expressing specific epitopes or via innate immune response towards structural mRNA parts. For example, RIG-1 binds 5'-triphosphate ends of RNA and triggers a signal cascade which results in activation of transcription factors and release of cytokines as parts of an antiviral response. Application of mRNA for stimulation of an immune response can be used in novel approaches to treat cancer, AIDS and to generate vaccines against almost any disease (cf. Pardi, N. et al., *Nat. Publ. Gr.* 543, 248-251 (2017) and Schlake T. et al., *RNA Biol.* 9, 1319-30 (2012)). Key to these exciting developments is the robust in vitro production of stabilized mRNA with improved translation efficiency and its delivery into cells using special transfection formulations.

mRNA stability and translation efficiency depend on several factors. Especially the untranslated regions at either ends of the mRNA play a crucial role. In eukaryotic protein expression, a cap structure at the 5'-end and the poly(A) tail at the 3'-end both increase mRNA stability and enhance protein expression. In addition, the 5'-UTR contains a ribosome binding site necessary for translation and the 3'-UTR contains RNA sequences that adopt secondary structures which improve stability and influence translation. Moreover, modified natural, e.g. N1-methylpseudouridine, and artificial nucleotides can be incorporated to improve mRNA stability and enhance translation of the mRNA (Svitkin Y. V. et al., *Nucleic Acids Research*, Vol. 45, No. 10, 6023-6036 (2017)).

Delivery of mRNAs into cells can be achieved by providing mixtures containing lipids for fusion with the cellular membrane and cations to neutralize the negative charge of the oligonucleotide backbone. Special formulations have been created to optimize mRNA delivery and to confer sufficient in vivo stability for clinical trials. Most of the mRNA formulations which are applied intravenously are taken up by and are expressed inside liver cells. This is due to the fact that the liver plays a major role in fatty acid metabolism and a high lipid content of the mRNA formulations therefore displays an organ-specific targeting effect. In most cases the liver is, however, not the desired target and therefore efforts are being made to modify lipid formulations to target organs, which are involved in an immune response, like e.g. the spleen (Kranz L. M. et al., *Nature* 534, 396-401 (2016)). Alternatively, cells of the immune system (e.g. lymphocytes) can be isolated from a patients' blood and mRNA application is performed ex vivo to allow targeting. Most recently, tissue-specific targeting of mRNA using antibody fragment modified lipid formulations has been disclosed (Moffett H. F. et al., *Nat. Commun.* 8, 389 (2017)).

Despite the recent advances and developments regarding the therapeutic applicability of mRNA either directly or indirectly, i.e. via ex vivo transfection of cells and returning such transfected cells to a patient, further improving the stability of mRNAs and developing new options in the context of their use as therapeutics or drugs are objects of ongoing research. Moreover, it is desirable to provide methods that allow for a streamlined and efficient production of therapeutic mRNA. Further, there is still a need for advanced targeted delivery of mRNA for protein substitution and gene replacement therapies, especially in the context of the treatment of inherited diseases. It is also highly desirable to enable the monitoring of delivery and protein expression. Finally, exploring further options for exploiting the immune stimulatory effect of mRNAs in e.g. cancer therapy is another object of ongoing research.

SUMMARY OF THE INVENTION

The present invention is directed to providing solutions to the above-mentioned objects and relates inter alia to a new kind of mRNA modification. Such modification not only allows to stabilize mRNAs of interest for ex vivo application and for subsequent administration to a human patient, animal or plant, but also to easily attach detectable labels or functional groups which e.g. allows for targeted delivery of the modified mRNA to specific cells or tissues and to monitor such delivery.

In a first aspect, the present invention relates to modified mRNA which comprises a 5'-cap structure, a 5'-untranslated region (5'-UTR), an open reading frame region (ORF), a 3'-untranslated region (3'-UTR) and a poly(A) tail region, wherein the mRNA contains at least one of an alkyne- or azide modification in the nucleotides within at least one of the ORF, the 5'-UTR, the 3'-UTR and the poly(A) tail region.

In especially preferred embodiments of this first aspect of the present invention, the modified mRNA contains one or more of a detectable label and/or a functional molecule introduced via a click reaction of the modified mRNA with a correspondingly modified alkyne- or azide-containing detectable label or functional molecule.

In a second aspect, the invention relates to a process for producing the modified mRNA according to the present invention, wherein such process comprises in vitro transcription of mRNA from a DNA template in the presence of an RNA polymerase and a nucleotide mixture containing the nucleotides required for RNA transcription, wherein at least a part of the nucleotides in the nucleotide mixture is modified to contain an alkyne- or azide-modification at the nucleotide. In an alternative embodiment of this second aspect, the modified mRNA is produced via a fermentation process. In such process, eukaryotic or prokaryotic cells are transformed to contain the genetic information (e.g. plasmid) for producing the desired mRNA and alkyne- or azide-modified nucleosides, nucleotides or nucleotide prodrugs are included in the growth medium. In another alternative embodiment of this second aspect, the mRNA of the invention is produced synthetically, via solid phase or phosphoramidite synthesis.

A third aspect of the present invention relates to an enzymatic method for the preparation of a site-specifically modified mRNA of the invention which contains an alkyne- or azide-modification in a defined region of the mRNA, e.g. the poly(A) tail region only. Such process comprises performing a poly(A) polymerase addition reaction on an mRNA in the presence of adenosine triphosphate (ATP), wherein the ATP is at least partly alkyne- or azide-modified at the nucleotide.

In especially preferred embodiments of the second and third aspects of the invention, one or more of correspondingly alkyne- or azide-modified detectable labels and/or functional molecules are added under conditions to perform a click reaction to produce a modified mRNA comprising such detectable label(s) or functional molecule(s).

A fourth aspect of the present invention relates to a cell preparation, especially a preparation of cells of the immune system, which contains the modified mRNA of the present invention and is obtained by ex vivo transfection.

A fifth aspect of the present invention relates to pharmaceutical compositions which comprise as an active agent or as an immunologic adjuvant a modified mRNA of the present invention or a cell preparation which was obtained by ex vivo transfection to include such mRNA.

A still further and sixth aspect of the present invention is a modified mRNA according to the invention, of a cell preparation including such mRNA or of a pharmaceutical composition of the invention for use in mRNA-based therapeutic and/or prophylactic applications in a human or an animal.

The use of a modified mRNA of the present invention for transfecting plants or plant cells is a further, seventh aspect of the invention.

An eighth aspect of the invention relates to diagnostic compositions for in vitro or in vivo screening for the presence, delivery and/or distribution of the inventive mRNA in cells, tissues or organs, such compositions comprising a modified mRNA of the present invention containing or afterwards being modified with a detectable label, preferable a fluorophore or a radionuclide.

A ninth aspect of the invention relates to a kit of parts for preparing and/or delivering a modified mRNA of the present invention. In especially preferred embodiments, such kit also contains one or more of correspondingly alkyne- or azide-modified detectable labels or functional molecules to obtain modified mRNAs containing such detectable labels and/or functional molecules upon performing the click reaction between modified mRNA and modified label/functional molecule.

A tenth aspect of the present invention relates to a method for stabilizing RNA, especially mRNA, wherein an alkyne- and/or azide-modification is introduced by including at least one of the four standard types of nucleotides (ATP, CTP, GTP and UTP) and/or another alkyne- or azide-modified compatible nucleotide or pseudonucleotide (i.e. a nucleotide with false or unusual structure as compared to the standard types of nucleotides) in partly or completely alkyne- and/or azide-modified form during RNA synthesis and/or in a poly(A) polymerase addition reaction. A further stabilization can be obtained by coupling of the corresponding azide- and/or alkyne-modified molecules or groups to the modified RNA via a click reaction.

An eleventh aspect of the present invention is a method for qualitatively and quantitatively determining at least one of the delivery to and expression of an mRNA of the present invention in a transfected cell via fluorescence-activated cell scanning (FACS).

DETAILED DESCRIPTION OF THE INVENTION AND PREFERRED EMBODIMENTS

The present invention employs so-called "click chemistry" or elements thereof and applies this technique to modify mRNA molecules to impart improved stability and/or to provide for use of such modified mRNA molecules in the context of inter alia mRNA based therapy and mRNA vaccine technologies.

Click chemistry is a concept which was defined in 2001/2002 by the groups of Sharpless and Meldal (Sharpless, K. B. et al., *Angew. Chem.* 2002, 114, 2708; *Angew. Chem. Int. Ed.* 2002, 41, 2596; Meldal, M. et al., *J. Org. Chem.* 2002, 67, 3057). Since then, especially the copper catalyzed reaction of azides with alkynes to give 1,2,3-triazoles, a variation of the 1,3-dipolar Huisgen cycloaddition (R. Huisgen, 1,3-Dipolar Cycloaddition Chemistry (Ed.: A. Padwa), Wiley, New York, 1984), has become a very widely used method to perform a click reaction. As a result of its mild conditions and high efficiency, this reaction has found a myriad of applications in biology and material sciences, such as e.g. DNA labeling for various purposes (Gramlich, P. M. A. et al., *Angew. Chem. Int. Ed.* 2008, 47, 8350).

In addition to the copper-catalyzed click-reaction, also copper-free, bio-orthogonal methods have been developed and all such methods can generally also be employed in the context of the present invention. E.g., strain-promoted azide-alkyne cycloaddition (SPAAC) (I. S. Marks et al., *Bioconjug Chem.* 2011 22(7): 1259-1263) can be used either alone or in combination with copper-catalyzed click chemistry (CuAAC) in the context of the present invention. Especially in cases in which it is desirable to perform a labelling reaction in vivo in cell culture or in a living organism, performing such reaction using SPAAC is preferable since the method does not require the use of toxic substances or external catalysts.

Click chemistry facilitates attaching reporter molecules or labels to biomolecules of interest and is a very powerful tool for identifying, locating, and characterizing such biomolecules. The method for example enables inclusion and attachment of fluorescent probes for spectrometric quantification, or of anchor molecules to allow for separation and purification of the target biomolecules. Up to date, many applications have been developed in which click chemistry is used as an underlying principle. Next-generation sequencing is one of such applications which benefits from this technique where formation of so-called "backbone mimics", i.e. non-natural alternatives for the phosphodiester bond, which can be generated by copper-catalyzed azide alkyne cycloaddition (CuACC), is used to ligate e.g. DNA fragments and adapter sequences. Despite the presence of a triazole ring instead of a phosphodiester bond, such backbone mimics are acceptable substrates for polymerase driven DNA or RNA preparation methods like PCR or reverse transcription. Detection of cell proliferation is a further field of application for click-chemistry. The methods that are normally applied include adding either BrdU or radioactive nucleoside analogs to cells during replication and detecting their incorporation into DNA. Methods involving radioactivity, however, are rather slow and not suitable for rapid high-throughput studies and are also inconvenient because of the radioactivity involved. Detecting BrdU requires an anti-BrdU antibody and applying denaturing conditions resulting in degradation of the structure of the specimen. The development of EdU-click assays has overcome such limitations by including 5-ethynyl-2'-deoxyuridine, a thymidine analog, in the DNA replication reaction. The detection via click chemistry instead of an antibody is selective, straight forward, bioorthogonal and does not require DNA denaturation for the detection of the incorporated nucleoside.

Within the context of the present invention it was discovered that it is possible to introduce alkyne- and/or azide-modified nucleotides during in vitro transcription of mRNA or during a fermentation process for producing mRNA to result in a correspondingly modified mRNA. The alkyne- or azide-modification can be included in only some or all elements contained in the mRNA, and needs to be included in at least one of the UTRs, ORF and poly(A) tail. The 5'cap structure preferably does not contain such alkyne- or azide modifications, as changes to the cap structure can interfere with efficient binding of initiation factors like eIF4E, eIF4F and eIF4G and thus drastically decrease translation efficiency. The presence of such modification on the one hand stabilizes the mRNA and on the other hand provides specific anchor sites for post-enzymatic labeling or for attachment of tissue- or cell-specific ligands or targeting molecules via click chemistry. Thus, the present invention not only enables detection of the presence and the location of mRNA after transfection or application, but also provides new options for targeted delivery of mRNAs to specific organs or cell types in the context of therapeutic applications. A correspondingly modified mRNA is a first subject matter of the present invention.

Depending on which type of nucleotide or nucleotides are included in alkyne- or azide-modified form during in vitro transcription or during mRNA production in prokaryotes or eukaryotes via fermentation, the resulting modified mRNA can contain modifications not only in the 5'- and 3'-UTRs and the ORF, but also in the poly(A) tail region. As apparent to the skilled person, including e.g. one or more of modified CTP, GTP and UTP leads to a modification within the UTRs and the ORF, while additionally including modified ATP results in a modification also of the poly(A) tail region. Including only alkyne- and/or azide-modified ATP during the transcription leads to modifications in the UTRs, the ORF and the poly(A) tail region.

No severe negative effects caused by the presence of alkyne- or azide-modified nucleotides within the mRNA of the invention have been observed. Depending on the amount of modified nucleotides included in the reaction, the in vitro and in vivo transcription efficiency can be as effective as in cases where only non-modified nucleotides are present in the reaction mixture, or slightly decreased. Furthermore, the modification of the mRNA does not seem to impair translation of mRNA during protein production at the ribosomes. Depending on the circumstances, the amounts of modified nucleotides to be included in the in vitro transcription reaction or the fermentation process can be adjusted to either provide maximum mRNA yield or maximum modification. For instance, when a dye is to be attached to the mRNA as a detectable label via a click reaction, it might be desirable to include an adequately high amount thereof to ensure and facilitate detection, whereas in order to target specific cell receptors, it might be sufficient to include only one or a few respective ligand molecules to achieve the desired effect.

As will be explained later in more detail, including alkyne- or azide-modified nucleotides has a stabilizing effect on mRNA. It is to be expected that the stabilizing effect of the inventive modification is most pronounced if such modification is distributed over the complete mRNA molecule. In such case, subsequent attachment of detectable labels and/or functional molecules via click chemistry will occur also uniformly over the whole mRNA molecule and can even provide for an enhanced stabilizing effect.

However, in some cases it may be important to restrict the inclusion of labels or functional molecules to a part of the mRNA molecule which is not involved in subsequent translation of mRNA during protein expression. For such purpose, it can be desirable to include modified nucleotides in the poly(A) tail region only whereby it can be ensured that ribosomal activity is not impaired by the presence of especially longer or bulkier labels or functional molecules like ligands or targeting molecules.

The present invention therefore also provides a modified mRNA containing alkyne- or azide-modification in the poly (A) tail region only. Instead of including alkyne- or azide modified nucleotides during in vitro transcription of a DNA template or a fermentation process, a modification in only the poly(A) tail region can be achieved for any desired mRNA by performing an addition reaction in the presence of poly(A) polymerase and alkyne- or azide-modified ATP.

By controlling the amount and type of alkyne- or azide-modification in the modified mRNA of the invention it is possible to conveniently and easily adapt the resulting mRNA to impart stabilization and options for post-enzymatic attachment of molecules of interest as required and viable with regard to any intended application.

Within the context of the present invention the azide- or alkyne-modification can be included at the nucleobase or at the 2'-position of the ribose unit of the respective nucleotide. In very special cases, inclusion of a nucleotide containing the modification at the 3'-position of the ribose is also possible. In such case, the enzymatic poly(A) addition reaction is terminated upon inclusion of one modified nucleotide. In one preferred embodiment of this aspect of the present invention, the modified mRNA contains an alkyne- and/or an azide-modification at the nucleobase or the 2'-ribose position in at least one of nucleotides within at least one of the UTRs, the ORF and optionally also the poly(A tail region, and additionally a chain-terminating alkyne- or azide-modification at the 3'-position of the ribose in the poly(A) tail. In a different preferred embodiment, the mRNA of the present invention does not contain a chain-terminating alkyne- or azide-modification at the 3'-ribose position in the poly(A) tail region.

The modified nucleotide included in the mRNA of the present invention can be derived from a natural nucleotide and especially one of the standard nucleotides with adenine, cytosine, guanine or uracil bases, or it can be a modification of another naturally occurring nucleotide (e.g. pseudouridine derivative) or even a non-naturally occurring molecule (e.g. F. Eggert, S. Kath-Schorr, *Chem. Commun.,* 2016, 52, 7284-7287) which does not negatively affect transcription and/or translation and the function of the resulting modified mRNA. Preferably the modified nucleotide is derived from a natural nucleotide or a naturally occurring nucleotide within mRNA.

Suitable alkyne- and azide-groups for click reactions are known and available to the skilled person and all such groups can be used to prepare modified nucleotides and modified mRNAs in the context of the present invention. The alkyne-modified nucleotide preferably is an ethynyl-modified nucleotide, more preferably 5-ethynyluridine phosphate or 7-ethynyl-7-deazaadenine phosphate. While it is in principle also possible to employ higher alkyne-modified nucleotides, especially propynyl or butynyl modified nucleotides and even C—C triple bond-containing ring systems, possible negative effects on e.g. the transcription or poly(A) polymerase reaction efficiency as well as on a further translation of the mRNA into a protein will have to be considered when selecting suitable alkyne molecules. Azido-modifications for nucleotides which are useful in the present invention can, e.g., also include azidoalkyl groups in which the alkyl part preferably is a lower alkyl group, especially a methyl, ethyl or propyl group. As an azide-modified nucleotide, preferably 5-(3-azidopropyl)-uridine phosphate or 8-azidoadenine phosphate are considered for inclusion in the inventive mRNA. An example for an azide-modified nucleotide causing termination of the poly(A) addition reaction is 3'-azido-2',3'-dideoxy adenine phosphate.

In principle, all nucleotides of the at least one type of modified nucleotide can be alkyne- or azide-modified, or alternatively, only a part of such nucleotides is present in modified form. In a preferred embodiment of the present invention and depending on the desired modification and modification rate, ratios of modified versus non-modified forms of the various nucleotides can range from 1:100 to 10:1, preferably 1:10 to 10:1, further preferably 1:4 to 4:1, and also preferably 1:2 to 2:1. Preferably, a 1:1, 1:4 or 1:10 combination of modified to non-modified nucleotide is included in the mRNA of the invention.

As mentioned above, the presence of alkyne- or azide-modified nucleotides or nucleobases in the modified mRNAs of the present invention confers a stabilizing effect. On the one hand, the attack of endoribonucleases is restricted to some extent by an internal modification. Extension of the poly(A) tail region during poly(A) polymerase based addition of modified ATPs at the 3'-end leads to a further stabilizing effect. Attack on and degradation of mRNA molecules by exoribonucleases occurs at the two ends of RNA. The mRNA according to the invention contains a cap at the 5'-end which provides protection from degradation at that side. Including additional modified adenosine nucleotides at the 3'-end imparts further protection as the attack of exoribonucleases in 3'→5' direction is impeded and degradation reaching the core mRNA, especially the ORF, is delayed.

In a preferred embodiment of the present invention, detectable labels and/or functional molecules can be introduced into the modified mRNA via click reaction with a correspondingly modified alkyne- or azide-containing label or functional molecule. As for the nucleotide modification, also for the modification of detectable labels or functional groups, suitable alkyne- and azide groups are known to the skilled persons and the preferred examples for such groups are applicable as described above. The reaction of an alkyne-modified nucleotide within the modified mRNA and an azide-containing label or functional molecule or the reaction of an azide-modified nucleotide within the modified mRNA of the invention and an alkyne-containing label or functional molecule is performed under conditions to conduct the click reaction and leads to formation of the 5-membered heterocyclic 1,2,3-triazole moiety which forms the link between mRNA and label or functional molecule. According to the present invention, the term alkyne-containing label or functional molecule also encompasses C—C triple bond-containing ring systems like cyclooctynes which have been considered especially in the context of SPAAC reactions and in vivo labelling via bio-orthogonal ligation reactions.

The type and size of labels and functional molecules are not particularly restricted and, again, are determined by the intended use. Preferred examples for the detectable label include color imparting or a fluorescence imparting labels, e.g. fluorescein derivatives like FITC, Alexa Fluor dyes or DyLight Fluor dyes, cyanine dyes like Cy5 and Cy3 or rhodamine dyes like Texas Red and 5-TAMRA, or any other fluorescent dye. Even non-colored small molecules can be used (e.g. biotin), when they are substrates for an enzyme or a binding protein-enzyme conjugate (e.g. antibody enzyme conjugates) and can produce a colored or luminescent product through an enzymatic reaction cascade and a further substrate. Also, radionuclides can be included as detectable labels, e.g. preferably positron emitting radionuclides which can be detected using positron emission tomography scan. For radionuclides with short half-lifes, e.g. $^{18}F$, the ability of quick and robust labeling of mRNA using a post mRNA production click labeling could be the only feasible method to obtain material for mRNA biodistribution studies using PET. Depending on the intended use, also heavy isotopes like $C^{13}$ or $P^{33}$ can be considered as a detectable label for the present invention.

Functional molecules to be included in the modified mRNA via a click reaction are not restricted and are preferably cell- or tissue-specific ligands that mediate targeted uptake of the mRNA into specific tissues or cells including cancer cells or at least allow to attach or anchor the mRNA onto the cell-surface. Such cell- or tissue-specific targeting can be achieved for example by using specific antibodies or antibody fragments, peptides, sugar moieties, small molecules (e.g. folic acid) or fatty acid moieties as the cell- or tissue-specific ligands. Respective substances have been described for a large number of targeting applications and are available to the skilled person. Some preferred and exemplary targeting molecules are antibodies or antibody fragments or receptor ligands which target cell specific receptors like e.g. the epidermal growth factor receptor, folate which targets the folate receptor, apolipoproteins which target endogenous low-density lipoprotein receptors or arachidonic acid which targets the endogenous cannabinoid receptors. Also, the amino acid sequence RGD or similar sequences have been found to mediate cell adhesion and can also be considered as preferred ligands within the context of the present invention.

The presence of functional molecules attached to the mRNA can further increase mRNA stability against nuclease degradation and it has been shown that partial as well as full replacement of at least one of the natural nucleotides within the mRNA for an alkyne- or azide-modified analogue and even attachment of functional molecules thereto does not hamper translation of the mRNA molecule.

In addition to including either alkyne-modified or azide-modified nucleotides, it is also possible that an inventive modified mRNA contains at least one nucleotide in partially or completely alkyne-modified form and at least one other nucleotide in partially or completely azide-modified form. A further option is an mRNA including at least one type of nucleotide in partially or completely alkyne—as well as in partially or completely azide-modified form. Such mRNA contains two different anchor modifications to which different labels or functional molecules can be attached in a downstream post-enzymatic click reaction. For example, but without limiting to such specific embodiment, an alkyne-modified cell-specific targeting group as well as an azide-modified detectable label can then be attached resulting in another preferred embodiment of a modified mRNA according to the present invention.

It is also possible and preferred within the context of the invention to provide a modified mRNA containing at least an azide-modified nucleotide and an alkyne-modified nucleotide, wherein e.g. at the azide-modified nucleotide a detectable label or a functional molecule has been attached via a biorthogonal reaction, e.g. SPAAC in vitro, whereas the alkyne-modified nucleotide is available for a downstream in vitro labelling reaction via a CuAAC reaction. If CuAAC reaction conditions are applied to the double labeled mRNA (containing alkyne and azide functions), it is possible to circularize the mRNA, which is, e.g., a valuable alternative to using self-splicing introns (DOI: 10.1038/s41467-018-05096-6).

It is for example also conceivable for the inventive modified mRNA to contain one kind of modification in the UTRs and the ORF and another modification solely in the poly(A) tail. Such modification can be effected by performing first a transcription reaction to introduce one or more first types of modified nucleotide and then following up with a poly(A) polymerase reaction using a second type of modification-containing ATP.

It will be apparent to the skilled person that numerous modifications and combinations of modifications are possible in the context of the present invention. Further, it is also possible to include different labels or functional groups based on the presence of the alkyne- and/or azide-modifications on the mRNA molecule, but rather also by consecutive addition under click reaction conditions of different appropriately modified labels or functional molecules. Consequently, the present invention provides a vast number of options and a convenient modularity in order to adapt the modified mRNA to the intended use in an optimal manner.

Apart from including alkyne- and/or azide-modified nucleotides, the present invention generally also allows for other modifications in the nucleotides as far as such other modifications do not adversely affect mRNA production or the intended use of the resulting mRNA to an extent which is not acceptable when contemplating the intended use (i.e. the modification is compatible with the modified mRNA within the context of the invention). As an example of such other modified nucleotide or nucleotide derivative that can be included in the mRNA, pseudouridine-5'-triphosphate (pseudo-UTP) can be considered. Pseudouridine (or 5'-ribosyluracil) was the first modified ribonucleoside that was discovered. It is the most abundant natural modified RNA base and is often designated as the "fifth nucleoside" in RNA. It can be found in structural RNAs, such as transfer, ribosomal and small nuclear RNA. Pseudouridine has been shown to enhance base stacking and translation. Further, pseudouridine-5'-triphosphate is able to impart advantageous mRNA characteristics such as increased nuclease stability and altered interaction of innate immune receptors with in vitro transcribed RNA. Incorporation of pseudo-UTP and also further modified nucleotides, like N1-methylpseudouridine and 5-methylcytidine-5'-triphosphate into mRNA, have been shown to decrease innate immune activation in culture and in vivo while simultaneously enhancing translation (B. Li et al., *Bioconjugate Chemistry*, 2016, 27, 849-853 and Y. Svitkin et al., *Nucleic Acid Research*, 2017, 45, 6023-6036). Inclusion of these and other suitable and compatible nucleotides, nucleotide analogues or non-naturally occurring molecules as described earlier in this specification, in alkyne- or azide-modified or in non-modified form is therefore a further option and preferred embodiment of the present invention.

As apparent from the above description of the modified mRNA of this invention, a multitude of different options exist to prepare or adapt an mRNA molecule to be beneficially applicable for various purposes. The invention is not restricted to a particular type of mRNA, which can rather be chosen in accordance with any intended use thereof, especially in the applications described in general or in more detail above in the background section as well as in the following. The mere introduction of the alkyne- or azide-modification conveys enhanced stability to an mRNA molecule which can be administered to deliver genetic information for applications like protein replacement therapy or to deliver mRNA for immunostimulatory purposes or as an mRNA-vaccine. Further modifying the mRNA via downstream click-coupling of respectively modified labels or functional molecules provides further possibilities especially for screening delivery of the modified mRNA and/or to target delivery of the mRNA to specific cells or tissues e.g. in a gene replacement therapy or to improve pharmacokinetics (e.g. slower renal clearance by adding PEG labels).

Within the context of the present invention, the modified mRNA of the present invention can encode a functional protein of interest. Furthermore, the modified mRNA of the invention can encode a recombinant protein like a chimeric protein or any further combination of proteins, peptides or peptides and proteins which can be advantageously used for a desired purpose. Especially an mRNA encoding a recombinant fusion protein, e.g. an mRNA comprising a sequence encoding a first protein or peptide ligated in frame with a sequence encoding a second protein or peptide are considered within the context of the present invention. The second protein or peptide can, e.g., target a specific localization within a cell or a tissue. Especially when considering the monitoring of the delivery and the localization of the modified mRNA of the invention or of a protein encoded by the mRNA within a target cell, a fusion protein of the protein of interest with a reporter protein like the green fluorescent protein (GFP), the enhanced green fluorescent protein (eGFP) or with a protein or peptide tag, e.g. the snap tag, is considered as a further preferred embodiment of the invention. To this purpose, the modified mRNA of the present invention can be engineered to express the fusion protein as a single protein preferably including two or more different functions as exemplarily outlined above. By means of including linkers, spacers or cleavage sites for proteases, production of two or more separate proteins is equally conceivable.

In the preferred embodiment of expression of a fusion protein of a protein of interest and GFP or eGFP, localization of the fusion protein can easily be detected under a fluorescent microscope using appropriate filters. Further, detection and quantification of transfected cells and production of the protein is also possible via other methods, preferably via flow cytometry, especially fluorescence-activated cell sorting (FACS). Using the above-mentioned methods allows for a qualitative and quantitative screening for cells which include a fluorescent molecule which especially is either a label introduced via a click reaction or a peptide or protein (co-)encoded by the mRNA itself.

Within the context of the present invention, the modified mRNA of the present invention can be used together with substances which are required or preferably present for a certain application. For example, for ex vivo cell transfection but also for in vivo administration, substances which facilitate mRNA uptake by cells are preferably combined with the mRNA. Lipid formulations as well as nanocarriers (e.g. as described by Moffett et al., mentioned supra) can preferably be included in respective compositions and formulations within the context of the present invention. Accordingly, a mixture of substances containing the modified mRNA and at least one other substance as mentioned above, or a kit of parts in which the modified mRNA and at least one other suitable substance are provided in different containers for subsequent combined use are further subjects of the present invention.

When combined with one or more other active substances, especially one or more substances which trigger an adaptive immune response, the modified mRNA of the present invention can also act as an adjuvant to enhance an innate immune response and, thus, an overall immunogenic effect. The effectiveness of substances like e.g. protein- or peptide-based tumor vaccines benefits tremendously from being administered together with RNA adjuvants (e.g. Ziegler et al., *J. Immunol.* Jan. 11, 2107, 1601129; DOI:https://doi.org/10.4049/jimmunol.1601129, or by Heidenreich et al., *Int. J. Cancer.* 2015 Jul. 15; 137(2):372-84, DOI: 10.1002/ijc.29402). The further advantages which are inherent to the inventive modified mRNA as described above in detail, ensure that the adjuvant properties of a modified mRNA of the present invention are comparable or even more pronounced than for non-modified RNA, while the stability of the molecule is improved and further options like targeted delivery or inclusion of labels via click reaction open up further perspectives.

For the adjuvant application mentioned above, the modified mRNA of the present invention can be combined or complexed with other substances which are known to the skilled person as optional or mandatory in this context, preferably cationic or polycationic compounds (see e.g. WO2010/037408). Complex formation or combination with such other substance confers improved immunostimulatory properties and especially the complex formation with a cationic element provides for a particularly strong adjuvant effect and thus is considered a preferred embodiment of the invention.

When intended as an adjuvant, the mRNA of the present invention is not necessarily required to encode a functional protein or peptide, rather also such non-coding RNAs which contain an alkyne- or azide-modification and optionally further a functional molecule or a detectable label introduced via the click reaction, are included in the invention for this purpose.

WO2010/037408 describes an immunostimulatory composition comprising an adjuvant component comprising at least one (m)RNA preferably complexed with a cationic or polycationic compound, and at least one free (i.e. non-complexed) mRNA which encodes at least one therapeutically active protein, antigen, allergen and/or antibody.

In this context, while a modified mRNA of the present invention can be included as only the adjuvant component, also a combination of a modified (m)RNA of the present invention acting as adjuvant and a further modified mRNA of the invention to be translated into a protein, antigen, allergen and/or antibody can be combined. Also, for such uses, it can not only be taken advantage of the possibility for specific targeting and delivery to cells provided by the present invention but also of the stabilization conferred to the (m)RNAs by the modification as disclosed earlier herein.

Another subject of the present invention is a process for producing the modified mRNA of the present invention. According to a first process, mRNA is transcribed in vitro from a DNA template in the presence of an RNA polymerase, usually T3, T7 or SP6 RNA polymerase, and a nucleotide mixture containing at least the four standard types of nucleotides (ATP, CTP, GTP, UTP) required for mRNA transcription and optionally naturally occurring modified nucleotides, like e.g. N1-methylpseudouridine triphosphate, or even suitable artificial nucleotides. In addition, to improve the translation efficiency it is important to generate a 5'-cap structure, e.g. 7-methylguanylate for eukaryotes. At least a part of at least one of the standard nucleotides, naturally occurring modified nucleotide analogue or suitable artificial nucleotide analogues is modified to contain an alkyne- or azide-modification at the nucleotide.

Depending on which type of nucleotide is used for the process, the modification will be effected in the UTRs and the ORF only (for modified CTP, GTP or UTP, or their analogues) or in all of the UTRs, the ORF and the poly(A) tail (for modified ATP alone or in combination with one or more of modified CTP, GTP or UTP, or their analogues).

The conditions and methods to perform in vitro mRNA transcription (IVT) as well as a poly(A) polymerase addition reaction are well known to the skilled person (e.g. Cao, G. J et al, *N. Proc. Natl. Acad. Sci. USA*. 1992, 89, 10380-10384 and Krieg, P. A. et al., *Nucl. Acids Res.* 1984, 12, 7057-7070)

Such conditions and methods are not particularly critical as long as a satisfactory yield of modified mRNA is obtained. In this context, also the kind of DNA template used within the first described process is not particularly critical. Usually, DNA to be transcribed is included in a suitable plasmid, however it can also be used in linear form. Additionally, a DNA template usually contains a promoter sequence, especially a T3, T7 or SP6 promoter sequence.

During the process of producing the modified mRNA of the present invention, the obtained mRNA is preferably capped using well-known methods (Muthukrishnan, S., et al, *Nature* 1975, 255, 33-37). Required reactants for the capping are commercially available, for example A.R.C.A. (P1-(5'-(3'-O-methyl)-7-methyl-guanosyl) P3-(5'-guanosyl)) triphosphate, a cap analog) (Peng, Z.-H. et al, *Org. Lett.* 2002, 4(2), 161-164). Preferably, as an alkyne-modified nucleotide, ethynyl-modified nucleotides, most preferably 5-ethynyl UTP or 7-ethynyl-7-deaza ATP, are included in the process. As an azide-modified nucleotide, preferably 5-(3-azidopropyl) UTP, 3'-azido-2',3'-dideoxy ATP (at the 3'-end only) or 8-azido ATP is used.

Within the context of the present invention, it is preferred to perform the transcription process using T7 RNA polymerase and to provide the DNA template in a suitable vector for efficient template production using microorganisms and subsequent in vitro transcription after linearization of the vector.

As an alternative to in vitro transcription, also a fermentation process in prokaryotic or eukaryotic systems for producing the mRNA of the invention is included in the context of the present invention. For this purpose, a DNA template, which is usually included in a suitable expression vector, preferably a plasmid containing the DNA of interest under control of an RNA polymerase promoter, is introduced into host cells or microorganisms and respective nucleosides or nucleotide prodrugs (to allow sufficient cellular uptake) as described above are included in the culture medium. Fermentative RNA production is known to the skilled person, cf. e.g. Hungaro et al. (J Food Sci Technol. 2013 October; 50(5): 958-964).

For illustration purposes, however not to restrict to such specific process, the production of alkyne-, azide- and click-modified mRNA via fermentation is described in more detail for a bacterial system: A DNA template, encoding the mRNA of interest under control of an RNA polymerase promotor, is introduced into bacterial cells. Preferably this is done via transfection of a plasmid. The design of the sequence is important and preferably contains all of several elements necessary for production of the desired mRNA: RNA polymerase promotor (e.g. T7 or SP6 promoter); the open reading frame of interest (ORF); and preferably also a sequence encoding the poly(A) region (preferably 100-120 nt long). Moreover, the plasmid contains an origin of replication and a selection marker for controlled growth and amplification in cell culture. It is preferable to have a gene regulatory element for the open reading frame, e.g. a lac operon, to selectively induce expression of the mRNA upon addition of an external compound. Important is the poly(A) region, necessary for discrimination of the mRNA from all the other RNAs (e.g. bacterial mRNAs, tRNAs and rRNAs) during purification and to provide the mRNA product with sufficient stability and translation efficiency. A poly(A) tail region can, however, also be introduced or a comparatively short poly(A) tail can be extended and possibly also modified via polymerase A addition reactions as described within the context of this invention after the fermentative production of the mRNA.

Alkyne- or azide modified nucleosides are added to the growing medium and are taken up by the bacterial cells via transporters or passive mechanism (J. Ye, B. van den Berg, *EMBO journal,* 2004, 23, 3187-3195). Intracellularly these nucleosides are phosphorylated by kinases to the corresponding triphosphates and can be incorporated into the mRNA. Since the monophosphorylation of the nucleosides is a slow process, it is possible to feed monophosphate prodrugs of the nucleosides to increase intracellular nucleotide concentrations (like for sofosbuvir).

In case of azide-modified mRNA, a click-reaction using biorthogonal chemistry, e.g. strain promoted azide-alkyne cycloadditions (SPAAC) can be performed in cell culture. Therefore, preferably cyclooctyne modified tags/labels or functional molecules are added to the medium.

The newly synthetized mRNA, which includes the modified nucleosides within the sequence, is then e.g. purified by the usage of poly(T) oligonucleotides attached to a specific resin and/or beads. e.g. of the mRNA isolation kit form Sigma Aldrich (cat No: 000000011741985001).

It is well known that the mRNA of prokaryotic cells does not contain a poly(A) region or when it does it is not longer than 20 nt, which is not enough to be taken up by the poly(T) oligonucleotides attached to the resin and/or beads, thus allowing for an efficient separation of the desired mRNA form prokaryotic mRNA. Thus, a fermentatively produced mRNA without a poly(A) tail regions or without a sufficiently long poly(a) tail region needs to be purified by other known methods via chloroform phenol extraction, precipitation and subsequent purification of the crude cellular RNA by ion exchange chromatography.

The bacterial strain, e.g. *E. coli* BL21(DE), needs to have the RNA polymerase, e.g. the T7 RNA polymerase, integrated in the genomic DNA (e.g. DE3 strains). Production of the mRNA is then possible when a plasmid containing the T7 promotor is transformed and can introduce the alkyne- or azide modified nucleoside during in vivo transcription within the bacterial cell.

It is well known that the prokaryotic mRNA is lacking the 5'CAP structure. This important element of the inventive modified mRNA can be introduced after the purification of the mRNA or it can be introduced concurrently by co-transforming the bacterial cell with another plasmid expressing the eukaryotic capping enzyme.

As a further alternative, it is possible to produce the modified mRNA of the present invention via solid phase or phosphoramidite synthesis and include modified nucleotides as described above. Especially in cases where the (m)RNA is intended for use as an adjuvant and shorter molecules or non-coding sequences can be considered for such purpose, synthetic preparation can be convenient and effective. Respective methods are available to the skilled person and described e.g. in Marshall, W. S. et al. *Curr. Opin. Chem. Biol.* 2004, Vol. 8, No. 3, 222-229.

A second process within the context of the present invention allows for modification of the poly(A) tail region only, by first providing an mRNA of interest by any suitable method and adding modified alkyne- or azide-modified ATP (or analog) in a poly(A) polymerase addition reaction. Such poly(A) polymerase addition reactions and suitable conditions are well-known to the skilled person and respective reaction kits are commercially available.

While the first and the second process described above can be used separately to provide modified mRNA of the present invention, it is also possible to use a combination of in vitro transcription or synthetic mRNA production and poly(A) polymerase addition reaction to include modified alkyne and/or azide-modified nucleotides in the UTRs, the ORF and the poly(A) tail during the mRNA transcription step. By additionally performing the second process, i.e. a poly(A) polymerase addition reaction, a further extension of the poly(A) tail can be achieved, wherein ATP is at least partly included in an alkyne- or azide-modified form which optionally is different from the modification that is introduced by the first process.

In case of a fermentative production of an mRNA in prokaryotes with or without a poly(A) tail region it is also possible to include a poly(A) polymerase addition reaction in order to provide such poly(A) tail or to extend an existing poly(A) tail region. In such embodiment, including modified adenine nucleosides or adenine nucleotide prodrugs for the reaction in the feeding medium is a preferred option. Alternatively, modified nucleoside triphosphates for the mRNA fermentation process can be internalized directly using either expression of nucleotide transporter proteins (D. A. Malyshev, K. Dhami, T. Lavergne, T. Chen, N. Dai, J. M. Foster, I. R. Correa, Jr., F. E. Romesberg, Nature 2014, 509, 385-388.) or by adding artificial molecular transporters in the feeding medium (Zbigniew Zawada et al., Angew. Chem. Int. Ed. 2018, 57, 9891-9895).

The processes for producing the mRNA of the invention can be performed using only one type of modified nucleotide or including one or more nucleotides comprising desired alkyne- or azide-modification. Within the context of the present invention, it is preferred to include one or two types of equally modified nucleotide, most preferably alkyne- or azide-modified uracil or adenine. As far as the alkyne-modification is concerned, it is most preferable to include an ethynyl group which, due to its size, is least prone to negatively affect the transcription reaction.

In another preferred embodiment of the invention, two differently modified nucleotides are included with the nucleotide mixture during transcription. Such a process results in a modified mRNA molecule which contains an alkyne—as well as an azide-modification.

No particular restrictions have been observed concerning the amount of modified nucleotides to be included during transcription or fermentation or via poly(A) polymerase reaction. Theoretically, all nucleotides employed in the in vitro transcription can be modified to contain alkyne- or azide-modified nucleobases. It is, however, preferred to use one or two types of modified nucleotides and also to include such nucleotides in modified as well as in non-modified form. Depending on the desired modification rate, it is preferred to include modified versus non-modified forms of the various nucleotides in a ratio of 1:100 to 10:1, preferably 1:10 to 10:1 and further preferably 1:4 to 4:1 or 1:2 to 2:1. Most preferably, only one type of modified nucleotide is employed which can be present in modified form only, or in combination with the non-modified form in the above-mentioned ratios. Preferably, a 1:1, 1:2 or 1:10 combination of modified to non-modified nucleotide is provided.

The ratios for introduction of modified nucleotides correspond with the number of modifications present in the inventive mRNA. Accordingly, the ratio of modified to non-modified nucleosides within the mRNA or the various parts, i.e. the UTRs and the ORF, or the UTRs, the ORF and the poly(A)tail, or the poly(A) tail alone is also preferably 1:100 to 10:1, more preferably 1:10 to 10:1 and further preferably 1:4 to 4:1 or 1:2 or 2:1, as well as most preferably 1:1, 1:2 or 1:10.

It is further possible and can be desirable to include differently modified natural nucleotides, e.g. pseudouridine or N1-methyl-pseudouridine and/or artificial nucleotides or nucleotide derivatives to improve mRNA stability and enhance translation of the produced mRNA. More information with regard to differently modified nucleotides and their incorporation into mRNA during in vitro transcription can be derived from Svitkin, Y. V. et al., *Nucleic Acids Research* 2017, Vol. 45, No. 10, 6023-6036.

Modified mRNA of the invention which is produced by in vitro mRNA transcription, by poly(A) polymerase addition reaction on an existing mRNA of interest, by a fermentation process or even completely synthetically and which comprises at least one of an alkyne- or azide-modification can further be modified via a click reaction to incorporate other molecules of interest, especially labels and/or functional molecules as already explained above. For example, detectable labels like e.g. fluorescent or colored molecules or non-colored molecules as mentioned earlier can be introduced. Also, as explained above, providing a modified mRNA to produce a fusion protein including, e.g., GFP or eGFP is another preferred option to include a detectable signal. As a consequence, e.g. delivery and/or expression of the generated mRNA can be monitored using fluorescent microscopy, FACS or other detection methods, especially in cell culture experiments. It surprisingly has been observed that even relatively big modifications of the bases within the ORF are accepted during translation of mRNA at the ribosome. For example, Cyanine 5 modified eGFP (enhanced green fluorescent protein) mRNA is commercially available (TRILINK biotechnologies, product code LL7701) that contains Cyanine 5 (Cy5) modified uridines. Such mRNA is readily translated to a functional protein in cell culture.

Selective modification of solely the poly(A) tail region can be achieved as described above, when poly(A) polymerase adds azide- or alkyne-modified ATP or ATP derivatives to the mRNA. Subsequent click labeling of this modified poly(A) tail has only minor effects on translation (as the sequence is not translated) and can be used, e.g. for tissue-specific ligands that mediate targeted uptake of the mRNA or to increase mRNA stability against nuclease degradation, as explained above. Especially in cases in which it is desired to attach very large molecules or molecules that due to other reasons impair translation, coupling via the poly(A) tail can be a preferred or even a mandatory approach.

The click reaction is well known to the skilled person and it is generally referred to Sharpless et al. and Meldal et al., mentioned supra. The overall conditions for the click reaction are described in these documents and it is further referred to disclosure in Himo F. et al., *J. Am. Chem. Soc.*, 2005, 127, 210-216, which relates to the preferred copper-catalyzed azide-alkyne cycloaddition (CuAAC). It is also referred to EP 2 416 878 B1 with regard to the conditions and reactants for the click reaction as well as to EP 17 194 093, wherein a preferred method for coupling a first molecule to a second molecule in a click ligation reaction is described. In this context, the copper-catalyzed click reaction is preferably performed in the presence of divalent metal cations in the reaction mixture, most preferably in the presence of $Mg^{2+}$.

While the above-mentioned documents describe click reactions in the context of ligating DNA molecules, in general, the same conditions can be applied within the context of the present invention. Thus, the click reaction is preferably carried out in the presence of a heterogeneous Cu (I) catalyst. Further, it is preferred to include a Cu (I) stabilizing ligand and/or organic solvents, especially DMSO to improve the efficiency of the click reaction, and/or divalent cations (e.g. as disclosed in PCT/EP2018/076495).

In a further preferred embodiment, the click reaction is performed as a strain-promoted azide-alkyne cycloaddition reaction (SPAAC) as described earlier with regard to the modified mRNA of the invention. The exact conditions of a CuAAC or a SPAAC reaction can be adapted to the individual circumstances as long as the basic requirements that are known to the skilled person are observed. As mentioned above, SPAAC can also be performed inside of cells. Introducing an alkyne- or azide-modified label into such cells can be useful in order to, after transfection of a modified mRNA into cells, monitor e.g. the location of the mRNA in the cell.

The present invention allows to produce in a modular and highly efficient manner modified mRNA molecules which contain modifications which impart a stabilizing effect on the mRNA. The modifications are also useful as anchor molecules to which other substances and molecules can be linked via a click reaction. Such click reaction is preferably performed downstream and separately from the transcription reaction which is a tremendous advantage, especially where large and bulky molecules of interest are to be ligated to the mRNA, which would completely disrupt the transcription reaction.

Within the context of the present invention, it can be sufficient that only a small set of alkyne- and/or azide-modified nucleotides are incorporated during in vitro mRNA production to allow synthesis of a whole range of densely modified mRNAs. This allows for a fast preparation and screening of many modifications. Moreover, the mRNAs of the present invention and processes for producing same permit to incorporate functional groups that are not readily or not at all accepted by the RNA polymerases during mRNA production but are easily attached via click reaction after transcription. Incorporation of such functional groups cannot be effected by conventional methods.

Thus, the inventive mRNAs and the processes for their production for the first time provide an easy and reliable method to produce stabilized and customarily modified mRNAs which can be labelled to follow-up on their uptake for example in ex vivo cell transfection and can also be modified to provide improved cell- or tissue-specific targeting for specific uses in therapy or vaccine preparation.

One preferred application of the mRNAs of the present invention lies in transfection of target cells ex vivo. As mentioned in the background section, mRNA formulations which are applied systemically and especially intravenously are taken up mainly by liver cells, whereas very often cells of the immune system are the preferred target in order to evoke an immune stimulatory effect or when mRNA is used for direct vaccination. In case that it is desired to incorporate the modified mRNA of the invention into specific cell types, such cells can be isolated from a patient, especially from a patient's blood, and mRNA transfection can be performed ex vivo.

A further subject of the present invention, therefore, is a cell preparation and especially a preparation of cells of the immune system, which includes a modified mRNA of the present invention and is obtained by ex vivo transfection of cells. In principle, the modified mRNA of the present invention can be used to transfect any kind of cell, human, animal or also plant cells. In one aspect of the invention, the cells of the cell preparation are of animal or human origin.

This aspect of the invention relates to inter alia adoptive cell transfer (ACT) and its manifold applications and uses which have been developed within the last decades. Autologous as well as non-autologous cells can be treated in order to for example improve immune functionality and other characteristics. Preferably, cells of the immune system are obtained from a patient and engineered to produce autologous immune cell which have been proven valuable in treating various diseases including cancer, e.g. B-cell lymphoma. The CAR-T cell based therapy is one such approach in which T-cells are genetically engineered to produce chimeric antibody receptors on their surface which recognize and attach to a specific protein or antigen on tumor cells.

The cell preparations of the present invention can be used in the same context. Depending on the modified mRNA which is introduced into cells, ensuing expression of a protein can provide for a multitude of effects of such cells after (re-)application to a patient. The present cell preparations, accordingly, are not restricted to a small number of applications but rather can be considered a vehicle for expression of mRNA in vivo after (re)application of cells which then produce a protein of interest and/or exert a certain effect (e.g. immune stimulating or tolerogenic) in the patient due to expression of the protein.

Methods for cell transfection are known to the skilled person and can be adapted to the particular cell type of interest. As an example for such process, it is referred to Moffett et al., mentioned supra. In the context of ex vivo transfection it is especially preferred to use an mRNA of the invention which is modified via click reaction to contain a cell-specific targeting group which facilitates uptake of the mRNA into the cell without transfection agents, since immune-cells are especially damageable by some of these transfection agent components.

In addition to ex vivo transfection of cells and administering such transfected cells to a patient, the modified mRNA of the present invention can also be applied directly to a patient. Both cases are considered a therapeutic (or also prophylactic) treatment. A further subject-matter of the present invention therefore is a pharmaceutical composition which comprises a modified mRNA or a cell preparation of the present invention as an active agent. As already mentioned, mRNA based therapeutics have recently become important research subjects. A large number of applications for mRNA as therapeutic agents has been described (e.g. Sahin et al, Schlake et al. and Kranz et al, all mentioned supra) and the modified mRNA of the present invention can not only be used in all such applications but can even provide for advantages and improvements thereto. Based on the enhanced stability of the modified mRNA and further based on an optionally present functional group, various problems can be solved. An enhanced stability accounts for e.g. a prolonged translation into protein compared to a non-modified mRNA. Further, the presence of a tissue- or cell-targeting group allows for targeted administration and high specificity of a therapeutic or immunogenic treatment.

Among suitable applications of the modified mRNAs, the cell preparations and the pharmaceutical compositions containing such mRNA or cell preparation are gene or protein replacement therapy, targeted transient gene delivery and genome engineering/gene editing (e.g. mRNA coding for a targeting endonuclease and a guide RNA like in the CRISPR/Cas9 system or similar), infectious disease vaccination, cancer immunotherapy, as well as cell-specific gene expression for a treatment of inherited diseases.

Gene replacement therapy can be considered for the treatment of a large number of diseases. For many diseases for which a deficiency or malfunction in a protein or enzyme is a leading cause or consequence, administration of the required active protein to the patient is essential to avoid immediate or consequential damage. However, continuous administration of proteins can cause intolerance or other negative side effects.

Furthermore, in order to provide sufficient amounts of a certain protein to a patient, high concentrations of such proteins need to be administered, sometimes as high as 100 mg/ml and up to 20 g of the protein per day and patient. As a further problem in protein replacement therapy, it can also be difficult to administer the protein into cells. On the other hand, it could be shown that for some mRNAs it is sufficient to provide 50 to 100 µg per dose to achieve a sufficiently high intracellular protein level in patients. Thus, the present invention and especially the possibility to target specific cells or tissues, provides a convenient solution to problems encountered with current protein replacement therapy approaches. By using modified mRNAs of the present invention in protein replacement therapy, it is for example in many cases sufficient to inject the mRNA whereas current protein replacement therapies require infusions which usually are time consuming and physically demanding for the patient.

Examples of diseases requiring protein replacement or at least constant protein supplementation include protein deficiency diseases, many metabolic diseases like type I diabetes, and also inherited disorders, especially lysosomal storage diseases like Morbus Gaucher or Morbus Hunter.

In the context of gene replacement therapy, including the modified mRNA into cells ex vivo as well as in vivo can be considered. Especially if a cell- or tissue-specific targeting-group is included with the mRNA of the invention, even in vivo insertion of the modified mRNA into target cells is expected to be highly efficient. The present invention allows for an endogenous translation of mRNA into protein, thus, avoiding adverse effects as mentioned above. Nevertheless, also ex vivo insertion of the mRNA into target cells and (re)administration of such target cells into patients is a further option within the context of the present invention, as mentioned above.

The pharmaceutical composition according to the invention can also be applied as mRNA vaccine. Vaccination is effected based on in situ protein expression to induce an immune response. Since any protein can be expressed from the modified mRNA of the present invention, the present pharmaceutical compositions can offer maximum flexibility as regards the desired immune response. Using the modified mRNA also provides a very fast immunization alternative compared to conventional methods for which it is necessary to produce various protein constituents or even inactivated viral particles. Conventional methods usually require performing different production processes whereas using the present invention, various mRNAs encoding different proteins or protein parts relating to the infectious agent can be produced in the same preparation process. Immunization by mRNA vaccination can even be achieved by single vaccinations and using only low mRNA doses. As opposed to DNA vaccines, RNA vaccines do not need to cross the nuclear envelope, but it rather is sufficient for them to reach the cell cytoplasm by crossing the plasma membrane. Further information regarding the development of mRNA vaccines is disclosed e.g. in Schlake et al., mentioned supra, and is applicable also in the context of the present invention. The pharmaceutical composition including the modified mRNA of the invention can be employed as prophylactic as well as therapeutic vaccines. The vaccines can be directed against any kind of pathogens, e.g. viruses like Zika virus which recently has become a major focus of attention (Pardi et al, mentioned supra).

In addition to a vaccination against exogenous pathogens, the pharmaceutical compositions of the present invention can also be used as anti-tumor vaccines or to stimulate the immune system within the context of cancer immunotherapy. Especially systemic RNA delivery to dendritic cells or macrophages offers the possibility to exploit antiviral defense mechanisms for cancer immunotherapy as described by Kranz et al., mentioned supra. Targeting e.g. macrophages or dendritic cells with an mRNA expressing a protein specific to or within the context of a certain type of cancer leads to presentation of parts of such protein by MHC molecules and elicits a potent and specific immune response. Accordingly, the modified mRNA of the present invention can also be used in the context of antigen-encoding mRNA pharmacology.

In the context of RNA-based immunotherapy and vaccination, it is especially preferred to include an (m)RNA adjuvant as described above in an immunostimulatory pharmaceutical composition. The adjuvant provides for a stimulation of the innate immune response and thus further enhances the immunotherapeutic effect. In this context, the modified mRNA of the present invention and the inventive (m)RNA adjuvant can have the same or a similar sequence and even encode the same protein. On the other hand, also a non-coding (m)RNA adjuvant or an (m)RNA adjuvant encoding a different protein or peptide can be combined to achieve the desired adjuvant effect.

Targeted gene editing using specific endonucleases and guide RNAs is a further application of the modified mRNA or pharmaceutical composition of the present invention. The recently developed, ground-breaking CRISPR/Cas9 technology enables specific gene editing, allows to introduce, delete or silence genes and is even able to exchange nucleotides within a gene. The method described by Charpentier and Doudna involves Cas-proteins which are ribonucleoproteins and endonucleases which bind to specific chemically synthesized CRISPR RNA (crRNA) sequences and cut DNA in the vicinity of such RNA sequences. In order to direct the endonuclease activity to the desired target DNA sequence, a so-called guide RNA is used which is complementary to the target DNA sequence. The guide RNA can take two forms, either a complex of a long, chemically synthesized trans-activating CRISPR RNA (tracrRNA) plus the crRNA, or a synthetic or expressed single guide RNA (sgRNA) that consist of both the crRNA and tracrRNA as a single construct. The modified mRNA of the present invention can be used in this context to encode one or both of the endonuclease and the guide RNA, preferably as a sgRNA which is complementary to a specific DNA sequence of interest.

The major advantage of the transient expression of the gene editing endonuclease and guide RNA from mRNA compared to the current technology, is the reduced risk of non-specific gene editing, since the gene expression of the genetic tool from mRNA is limited to a short period of time (a few days) and not constantly expressed from an integrated genome element.

Gene editing applications have high importance and can be applied in the context of a huge variety of therapeutic applications, e.g. gene replacement therapy, cancer therapy and treatment of inherited diseases. Use of the modified mRNA of the invention in the context of all such applications is included within the scope of the present invention.

Also for other potential therapeutic applications described for mRNAs in the prior art or which are developed in the future, use of respective mRNAs including the modifications as described herein is of advantage due to their improved stability. Further, including a tissue- or cell-specific targeting molecule to the mRNA via the downstream click reaction, allows for a more specific and accordingly more efficient use in therapy. Especially any desired protein expression or also any immunization reaction can be precisely targeted to the location in a patient where the therapeutic or immunizing effect is required.

A preferred embodiment of the pharmaceutical composition of the present invention includes the modified mRNA together with a pharmaceutically acceptable carrier, excipient and/or adjuvant, preferably a modified (m)RNA adjuvant as described above containing the same modification as the modified mRNA and which is complexed with a cationic or polycationic compound. In a further preferred embodiment, the pharmaceutical composition comprises complexing agents, which protect the mRNA further from degradation. The complexing agent may improve and enhance uptake by cells and concurrent translation into protein. As complexing agents, lipids or polymers can be included in the pharmaceutical composition. In a further preferred embodiment, the pharmaceutical composition can contain the modified mRNA encapsulated in liposomes.

In a further preferred embodiment, the pharmaceutical composition contains cationic lipids. Agents that further improve the delivery of nucleic acids to the cytosols can also be preferably included in the pharmaceutical compositions of the present invention. Such agents can be tailored to the specific route of delivery. In summary, the pharmaceutical compositions of the present invention, while including the inventive modified mRNA as active agent, can include any further substances for improving further the stability of the active substance, enhancing delivery to the cytoplasm of target cells and providing other complementary or synergistic effect.

Within the context of the present invention, a pharmaceutical composition is included which as an active agent contains a cell preparation, especially a preparation of cells of the immune system, which is obtained by ex vivo transfection of cells with a modified mRNA of the present invention. The transfected cells can be returned to the patients in order to benefit from the effects of the modified RNA included in the cells. Also for this preferred embodiment of a pharmaceutical composition of the invention, pharmaceutically acceptable adjuvants or excipients or carriers can be included as outlined before.

A further subject of the present invention is a diagnostic composition containing a modified mRNA of the present invention or a cell transformed with a modified mRNA of the present invention for in vitro or in vivo screening for the presence, delivery and/or distribution of the inventive mRNA in cells, tissues or organs. For such purpose, preferably the modified mRNA already includes a detectable label which was introduced via a click reaction. Such label preferably is a fluorophore or a radionuclide, preferably a positron emitting radionuclide. Detecting and possibly also quantifying the detectable label allows to observe and detect delivery of the modified mRNA to cells, tissues or organs, the distribution therein or to monitor the re-administration of cells into a patient. Accordingly, a diagnostic composition of the present invention contains a modified mRNA of the invention, preferably an mRNA containing at least one detectable label. Within this context, including a modified mRNA which upon expression produces a detectable protein, e.g. a fusion protein including a fluorescent protein, is a further preferred embodiment.

In a further aspect of the present invention and as mentioned earlier, also plant cells can be transfected using the modified mRNA of the present invention. Such transfected plant cells are also encompassed within the scope of the present invention. The modified mRNA can be included e.g. in order to introduce genetic information, especially for transient expression of certain proteins in such plant cells, or for analytic or diagnostic purposes e.g. as labeled probes. Conferring disease or pest resistance or tolerance are only some examples of possible applications and beneficial effects of introducing inventive mRNAs into plant cells or plants. The use of a modified mRNA of the present invention for transfection of plant cells or plants, accordingly, is also a subject of the present invention.

Still a further subject of the present invention is a kit for preparing a modified mRNA of the present invention. Such kit contains the various substances required for preparing the modified mRNA via in vitro transcription, a fermentation process or a poly(A) polymerase addition reaction, i.e. an RNA polymerase and/or poly(A) polymerase, alkyne- or azide-modified nucleotides as well as unmodified nucleotides and optionally further buffer substances and solvents or further substances required for the process. In preferred embodiments, also alkyne- and/or azide-modified detectable labels or functional molecules as well as substances required for performing the click reaction between the modified mRNA and the labels or functional molecules are included. Also, a kit for producing the modified mRNA of the present invention entirely synthetically is a further subject of the present invention. The required substances can be provided in separate containers or can be combined as far as no adverse reaction occurs between such combined substances. As regards the various substances to be included in such kit of parts, it is referred to the above description regarding the modified mRNA of the invention and the processes for preparing such modified mRNA. As far as production of the modified (m)RNA adjuvant is concerned, such kit preferably also contains a cationic or polycationic compound which according to a preferred embodiment is used to form a complex with the (m)RNA. The kits according to the present invention can also contain further substances facilitating the delivery of the modified mRNA of the invention to cells ex vivo or in vivo.

In preferred embodiments, a kit includes at least one modified mRNA of the invention, preferably containing a detectable label or a functional molecule introduced via click reaction, or it provides the modified mRNA and the alkyne- or azide-modified label and/or functional molecule and optionally other click reagents in separate containers.

In a further embodiment of the invention, a kit for delivery of the modified mRNA to a patient contains an mRNA and preferably also an (m)RNA adjuvant, both modified according to the present invention. The modified mRNA and the modified (m)RNA adjuvant can be contained in one single container or in separate containers and both can optionally include an alkyne- or azide-modified label or functional molecule either already attached via click reaction or in separate containers for subsequently performing the click reaction. The kit can further contain other pharmaceutically acceptable carriers and adjuvants, again either in separate containers or combined with at least one other constituent of the kit.

It will be apparent to the skilled person that many different combinations of substances can be included in kits which facilitate the preparation or the use of the modified mRNA of the invention. All embodiments and variations thereof described above in the context of the present invention are also applicable for the kits described here. All suitable combinations of substances are included for the purposes of the present invention.

A further subject of the present invention relates to a method for stabilizing RNA, especially mRNA, such method including introducing an alkyne- and/or an azide-modification by including at least one of the four standard types of nucleotides (ATP, CTP, GTP and UTP) in partly or completely alkyne- and/or azide-modified form during RNA synthesis and/or in a poly(A) polymerase addition reaction to produce a modified (mRNA). As described above, the modification of an RNA, especially an mRNA by including alkyne- and/or azide-modified nucleotides, and especially by optionally including also one or more of a detectable label and a functional molecule via a click reaction, results in a stabilizing effect on the RNA molecules. Thus, a corresponding method is considered a further important aspect included with the present invention.

Still a further subject of the present invention is an in vitro method for qualitatively or quantitatively determining the presence and/or expression of an mRNA according to the present invention in target cells. In this context, the transfection efficiency, a quantification of mRNA delivery and expression can be determined at a single cell resolution via FACS analysis. Fluorescence-activated cell sorting/scanning, FACS, is well-known to the skilled person. The fluorescent labels that can be introduced into the modified mRNA of the present invention via click-reaction can be determined based on this method. Furthermore, mRNA delivery and expression of the encoded protein can be detected using a fluorescent protein, e.g., the GFP protein or eGFP protein which in a preferred embodiment can be co-expressed with a protein of interest as a fusion protein or as two separate proteins, as described above.

Accordingly, using the FACS method, the influence of the modification on cell transfection and the expression level of the protein encoded by the modified mRNA of the invention can easily be determined. Also studying effects of different labels on the expression level can be performed via FACS analysis.

In such FACS analysis, e.g. a comparison of non-transfected cells and transfected cells allows to detect fluorescent signals which can be attributed to the fluorescent label included in the modified mRNA of the invention or the fluorescent protein expressed by translation of the modified mRNA of the invention. Also a comparison of transfection reactions of the same target cells with modified mRNA of the invention versus non-modified mRNA having the same nucleotide sequence can ensure that the modification per se does not negatively influence the transfection efficiency.

All information disclosed above with regard to one subject of the present invention is considered to equally apply in the context of other subjects for which this information, even if not explicitly repeated, has recognizable relevance within the context of the invention.

BRIEF DESCRIPTION OF THE FIGURES

FIG. 6 shows a map and the complete sequence (from T7 promoter to poly(A) end) of the plasmid used in linearized form as DNA template during the T7 RNA polymerase reaction in the Examples. The sequence is also referred to as SEQ ID NO: 2.

The following examples further illustrate the invention:

EXAMPLES

Example 1

Figure 1:
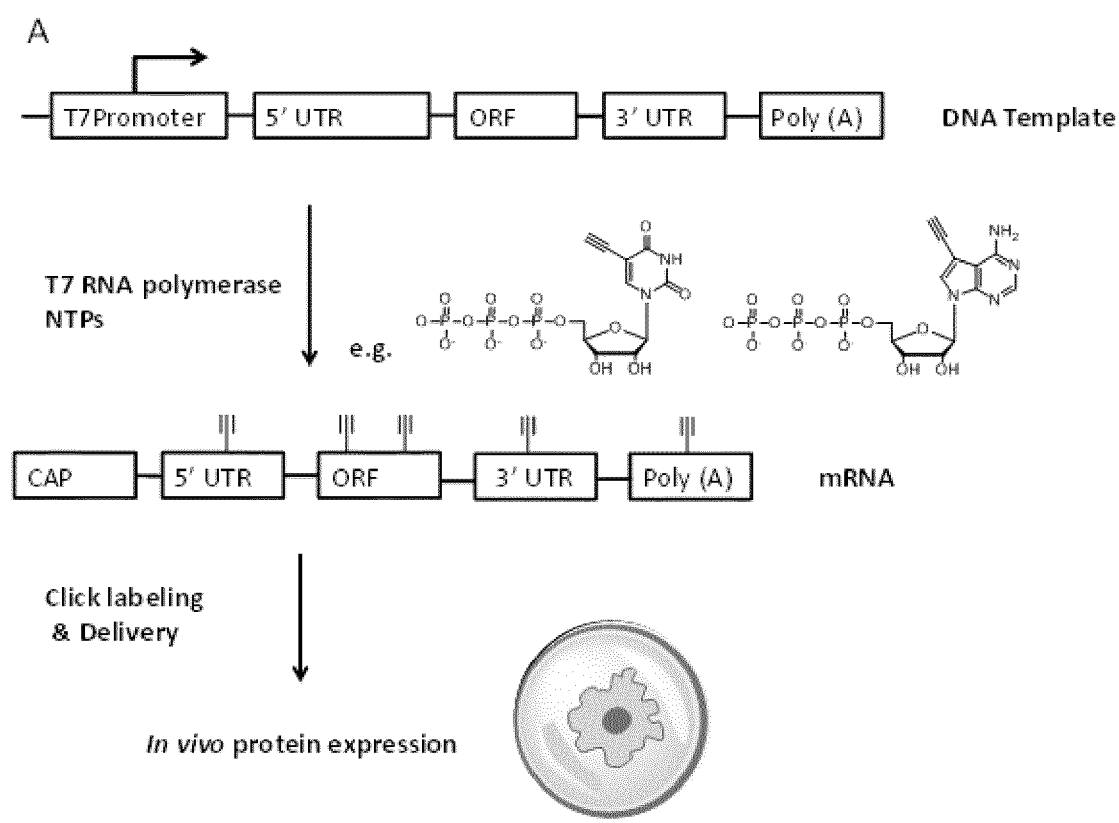
FIG. 1 shows a general scheme of modified mRNA production and application. Using e.g. 5-ethynyl UTP (EUTP) it is possible to insert alkyne groups available for click reaction with the 5'-UTR, 3'-UTR and the ORF. Selective labelling of the poly(A) tail is possible using e.g. 7-ethynyl 7-deaza ATP and a poly(A) polymerase.
Figure 2:
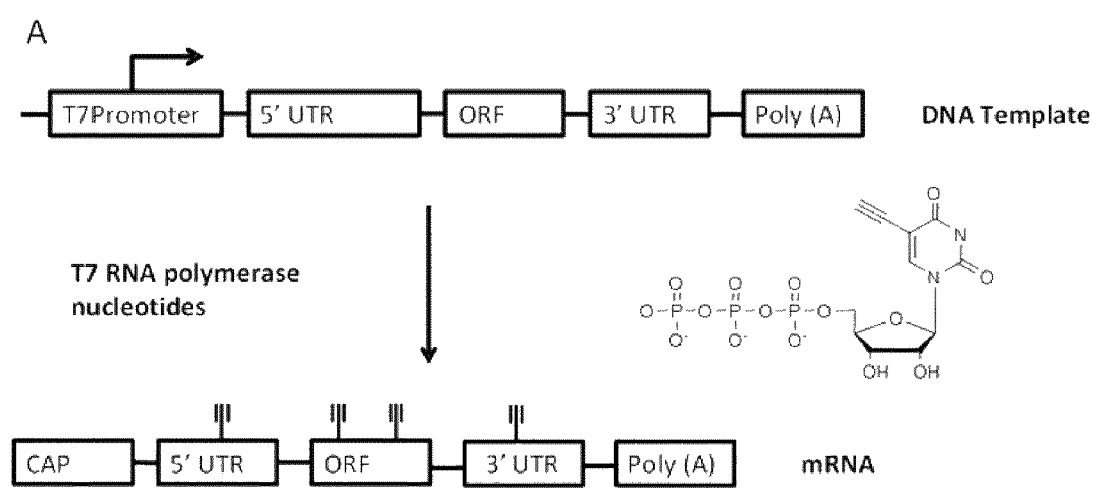
FIG. 2 shows the general schematic production of alkyne-modified mRNA using e.g. T7 RNA polymerase and a nucleotide mixture including EUTP (structural formula).

Alkyne-modified mRNA coding for the enhanced green fluorescent protein (eGFP) was produced by in vitro transcription (IVT) from a DNA template using T7 RNA polymerase and nucleotide mixtures. Here 5-ethynyl-uridine-5'-triphosphate (EUTP) was included in the nucleotide mixture to generate an alkyne-modified mRNA according to FIG. 2 for subsequent transfection into Henrietta Lacks' immortal cells (HeLa cells). The generated mRNA contains a 5'-cap, untranslated regions (UTR), the protein coding part (open reading frame, ORF) and a poly(A) tail.

mRNA Production

In a 50 µL reaction volume 20 units of T7 RNA polymerase, 1 µg of template DNA and several nucleotides were combined in transcription buffer (40 mM Tris-HCl, pH 7.9, 6 mM MgCl$_2$, 4 mM spermidine, 10 mM DTT).

A) Final nucleotide concentrations for non-alkyne modified mRNA production were:

1.0 mM GTP, 4.0 mM A.R.C.A. (P1-(5'-(3'-O-methyl)-7-methyl-guanosyl) P3-(5'-(guanosyl))triphosphate, Cap Analog), 1.25 mM CTP, 1.25 mM UTP, 1.25 mM ψUTP (pseudouridine triphosphate), 1.5 mM ATP.

B) Final nucleotide concentrations for alkyne modified mRNA production were:

1.0 mM GTP, 4.0 mM A.R.C.A. (P1-(5'-(3'-O-methyl)-7-methyl-guanosyl) P3-(5'-(guanosyl))triphosphate, Cap Analog), 1.25 mM CTP, 1.25 mM EUTP (5-ethynyluridine triphosphate), 1.25 mM ψUTP (pseudouridine triphosphate), 1.5 mM ATP.

C) Final nucleotide concentrations for alkyne modified mRNA production and subsequent click labeling were:

1.0 mM GTP, 4.0 mM A.R.C.A. (P1-(5'-(3'-O-methyl)-7-methyl-guanosyl) P3-(5'-(guanosyl))triphosphate, Cap Analog), 1.25 mM CTP, 0.625 mM EUTP (5-ethynyluridine triphosphate), 0.625 mM ψUTP (pseudouridine triphosphate), 0.625 mM UTP, 1.5 mM ATP.

The mixture was incubated for 2 hours at 37° C. and then 2 units of DNAse I were added and incubated for 15 minutes at 37° C. The mRNA was purified by a spin column method according to manufacturers' instruction for PCR products (PCR purification kit from Qiagen). This yielded 13.3 µg of mRNA for A, 12.3 µg B and 14.3 µg for C, which was directly used for transfection when no click labeling was needed (A and B). When click labeling was performed (C), 2 µg of RNA, 1 nmol Eterneon Red 645 Azide (baseclick GmbH), a single reactor pellet and 0.7 µL 10× Activator$^2$ (baseclick GmbH, Oligo$^2$ Click Kit) were combined in a total reaction volume of 7 µL. The reaction mixture was incubated at 45° C. for 30 min and then cleaned using a spin column method according to manufacturers' instruction for PCR products (PCR purification kit from Qiagen).

For transfection a commercial kit (jetMESSENGER™ from POLYPLUS TRANSFECTION®) was used according to manufacturers' instructions using 0.5 µg of mRNA and 25,000 HeLa cells (CLS GMBH) reaching confluence. The cells were incubated at 37° C. for 24 hours before analysis under the fluorescent microscope, GFP filter: (470/22 excitation; 510/42 emission) and Cy5 filter (628/40 excitation; 692/40 emission) were used.

Figure 3:
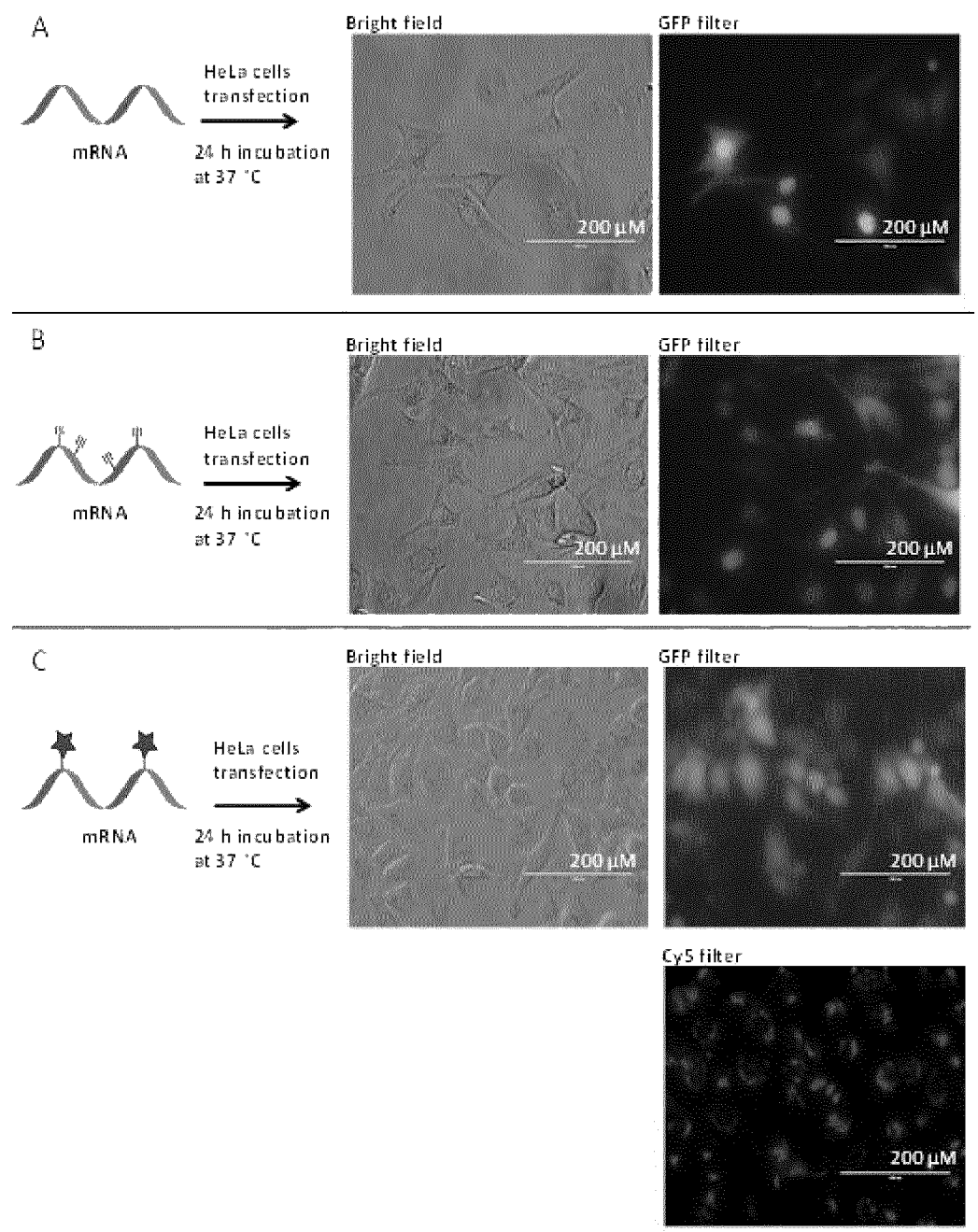
FIG. 3 shows the results of transfection of non-alkyne (A), alkyne (B) and dye (C) modified mRNA coding for eGFP into HeLa cells.

FIG. 3 shows the results of transfection of non-alkyne (A), alkyne (B) and dye (C) modified mRNA coding for eGFP into HeLa cells. After 24 h incubation at 37° C. green fluorescence of the eGFP was observed (GFP filter). For the Eterneon Red labeled mRNA (C) the localization of the mRNA was observed using Cy5 filter settings.

In the bright field image cell morphology of healthy HeLa cells was observed (FIG. 3, A-C), using the GFP filter protein expression of the eGFP was visible (exposure time 120 ms for A-B, 250 ms for C). For the click labeled mRNA (FIG. 3, C) also the localization of the mRNA was observed using the Cy5 filter settings of the microscope.

Supporting Information:

Structure of the modified nucleotides used during the T7 RNA polymerase reaction described above.

The map and complete sequence (from T7 promoter to poly(A) end) of the plasmid used in a linearized form as DNA template during the T7 RNA polymerase reaction described above is shown in FIG. 6. The sequence is also referred to SEQ ID NO: 2.

Example 2

Figure 4:
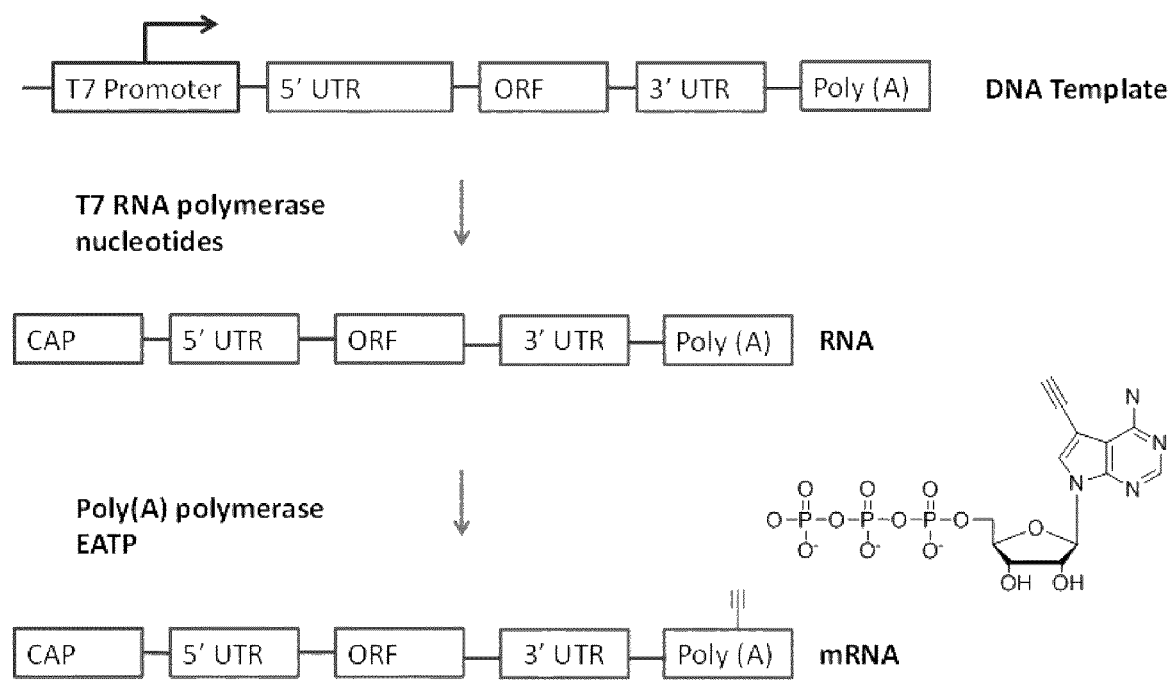
FIG. 4 shows the general schematic production of alkyne-modified mRNA using e.g. poly(A) polymerase and the alkyne modified nucleotide EATP (structural formula).

Alkyne-modified mRNA coding for the enhanced green fluorescent protein (eGFP) was produced by in vitro transcription (IVT) from a DNA template (FIG. 6) using T7 RNA polymerase and nucleotide mixtures. Here 7-ethynyl-adenine-5'-triphosphate (EATP) was incorporated in the IVT mRNA after the T7 RNA polymerase reaction by poly(A) polymerase to generate an alkyne-modified mRNA according to FIG. 4 for subsequent click labeling and transfection into Henrietta Lacks' immortal cells (HeLa cells). The generated mRNA contains a 5'-cap, untranslated regions (UTR), the protein coding part (open reading frame, ORF) and a poly(A) tail alkyne labeled.

mRNA Production

In a 50 µL reaction volume 20 units of T7 RNA polymerase, 1 µg of linearized template DNA and several nucleotides were combined in transcription buffer (40 mM Tris-HCl, pH 7.9, 6 mM MgCl$_2$, 4 mM spermidine, 10 mM DTT).

Final nucleotide concentrations for non-alkyne modified mRNA production were:

1.0 mM GTP, 4.0 mM A.R.C.A. (P1-(5'-(3'-O-methyl)-7-methyl-guanosyl) P3-(5'-(guanosyl))triphosphate, Cap Analog), 1.25 mM CTP, 1.25 mM UTP, 1.25 mM ψUTP (pseudouridine triphosphate), 1.5 mM ATP.

The mixture was incubated for 2 hours at 37° C. and then 2 units of DNAse I were added and incubated for 15 minutes at 37° C. The mRNA was purified by a spin column method according to manufacturers' instruction for PCR products (PCR purification kit from Qiagen). This yielded 12.3 µg of mRNA which was directly used for poly(A) polymerase reaction with EATP.

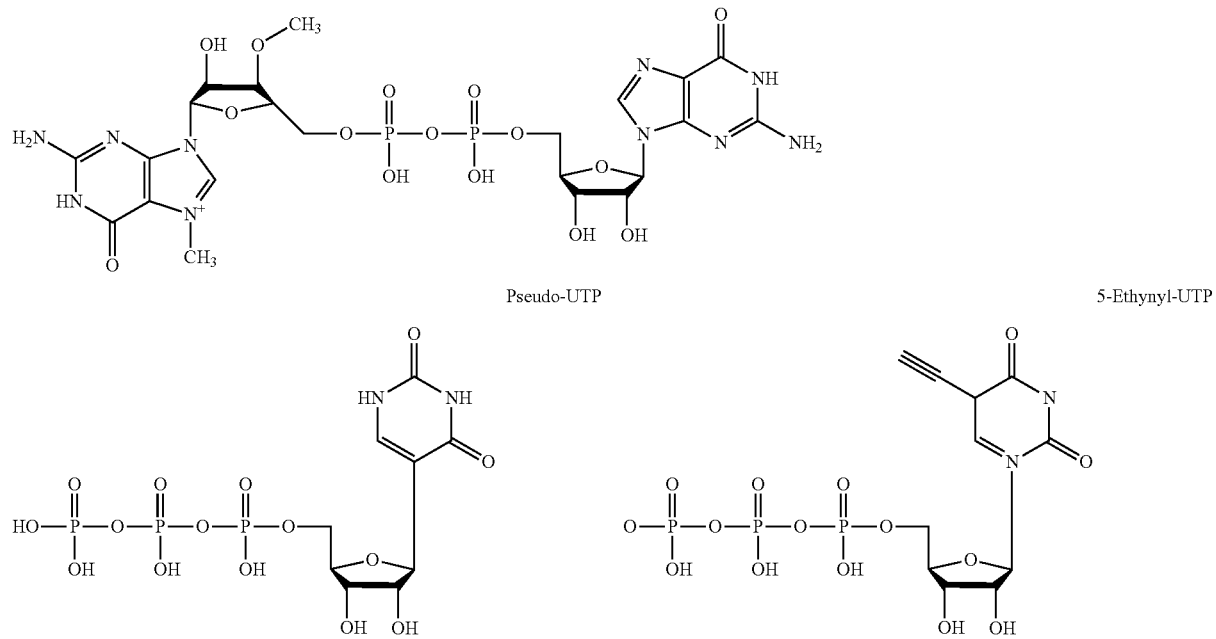

A.R.C.A.(P1-(5'-(3'-O-methyl)-7-methyl-guanosyl) P3-(5'-(guanosyl))triphosphate

Pseudo-UTP

5-Ethynyl-UTP

In a 20 µL reaction volume 5 units of *E. coli* poly(A) polymerase, 4.2 µg of mRNA prepared before and a solution of 1 mM EATP were combined in reaction buffer (250 mM NaCl, 50 mM Tris-HCl, 10 mM $MgCl_2$, pH 7.9)

The mixture was incubated for 1 hour at 37° C. The mRNA was purified by a spin column method according to manufacturers' instruction for PCR products (PCR purification kit from Qiagen). This yielded 4 µg of mRNA.

The click labeling was performed using 1.1 µg of RNA, 1 nmol Eterneon Red 645 Azide (baseclick GmbH), a single reactor pellet and 0.7 µL 10× Activator[2] (baseclick GmbH, Oligo[2] Click Kit) were combined in a total reaction volume of 7 µL. The reaction mixture was incubated at 45° C. for 30 min and then cleaned using a spin column method according to manufacturers' instruction for PCR products (PCR purification kit from Qiagen).

For transfection a commercial kit (jetMESSENGER™ from POLYPLUS TRANSFECTION®) was used according to manufacturers' instructions using 0.5 µg of mRNA and 25,000 HeLa cells (CLS GMBH) reaching confluence. The cells were incubated at 37° C. for 24 hours before analysis under the fluorescent microscope, GFP filter: (470/22 excitation; 510/42 emission) and Cy5 filter (628/40 excitation; 692/40 emission) were used.

Figure 5:
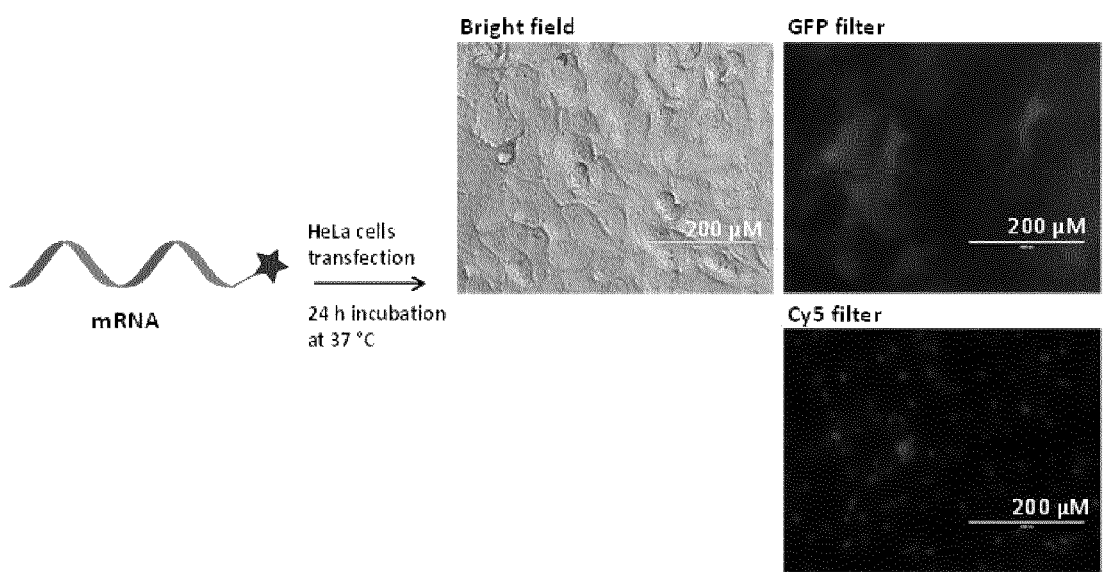
FIG. 5 shows the results of transfection of Eterneon-red 645 modified mRNA (alkyne modification in poly(A) tail only) coding for eGFP into HeLa cells.

FIG. 5 shows the results of transfection of Eterneon Red modified mRNA coding for eGFP into HeLa cells. After 24 h incubation at 37° C. green fluorescence of the eGFP was observed (GFP filter). For the Eterneon Red labeled mRNA the localization of the mRNA was observed using Cy5 filter settings.

In the bright field image cell morphology of healthy HeLa cells was observed (FIG. 5), using the GFP filter protein expression of the eGFP was visible (exposure time 120 ms). Localization of the mRNA labeled with Et-Red was observed using the Cy5 filter settings of the microscope.

Example 3

In order to prove incorporation of the EATP (Ethynyladenosine-5'-triphosphate) within the poly(A) tail a short RNA oligonucleotide (31 mer, CUAGUGCAGUACAU-GUAAUCGACCAGAUCAA, SEQ ID NO: 1) was used as template for the poly(A) polymerase reaction using:

A) 1 mM ATP
B) 1 mM EATP;
C) 0.5 mM ATP and 0.5 mM EATP.

In a 20 µL reaction volume 5 units of *Escherichia coli* poly(A) polymerase, 2 µg of RNA (31 mer) and nucleotide (final concentration of A-C) were combined in reaction buffer (250 mM NaCl, 50 mM Tris-HCl, 10 mM $MgCl_2$, pH 7.9). The mixtures were incubated for 30 minutes at 37° C. or for 16 hours at 37° C.

Figure 7:
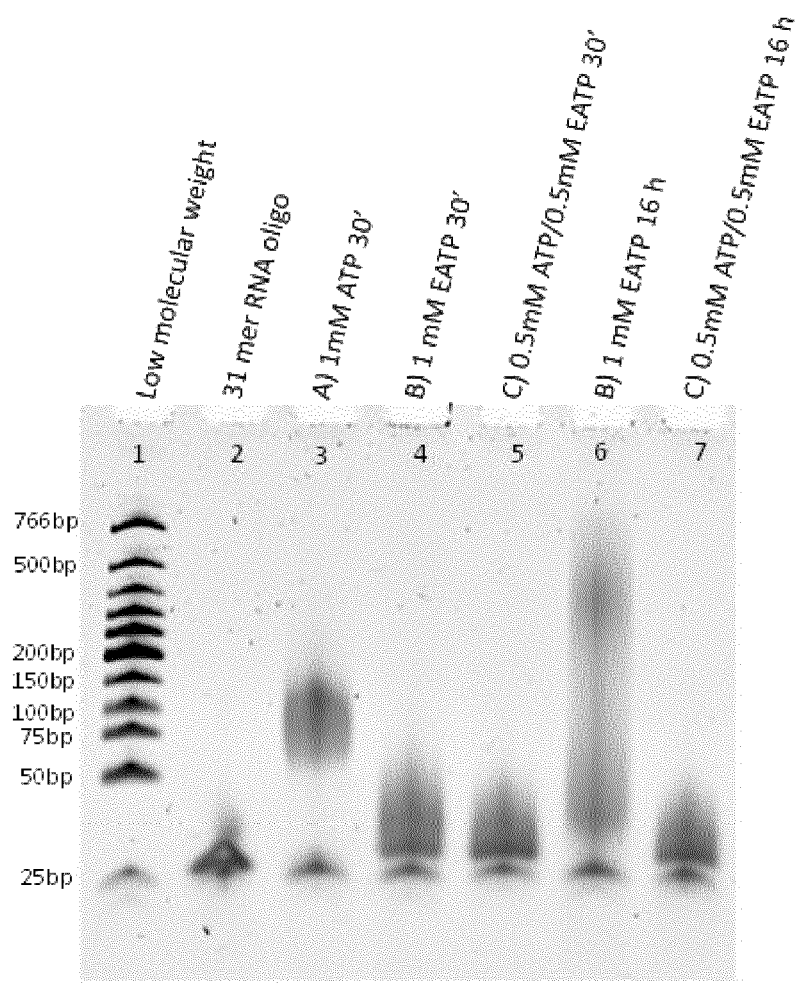
FIG. 7 shows the result of experiments to prove incorporation of EATP into the poly(A) tail of an RNA as described in Example 3.

The results were analyzed by denaturing polyacrylamide gel electrophoresis (7 M urea, 1×TBE, 7% polyacrylamide gel, constant voltage 100 V, 1 h). Compared to the template RNA oligonucleotide (FIG. 7, Lane 2) a band or smear at higher molecular weight appeared for all samples, which were incubated in the presence of the poly(A) polymerase using different nucleotides and incubation durations (FIG. 7, Lane 3-7). This indicated successful incorporation of ATP or its alkyne analog EATP. Within 30 min incubation the incorporation of ATP (FIG. 7, Lane 3) was more efficient compared to EATP (FIG. 7, Lane 4) or a mixture of EATP and ATP (FIG. 7, Lane 5). By extending the incubation time for the incorporation of EATP to 16 h, the length of the poly-EA-addition was increased (FIG. 7, Lane 6) in comparison to 30 min incubation (FIG. 7, Lane 4). Interestingly, for the nucleotide mixture containing ATP and EATP no change was observed after 16 h (FIG. 7, Lane 7) compared to 30 min.

FIG. 7 shows the ethidium bromide stained 7% denaturing polyacrylamide gel of different polyadenylation reactions as described above. In each lane 500 ng of RNA were loaded. Lane 1: low molecular weight DNA ladder (New England Biolabs), Lane 2: 31 mer RNA oligonucleotide template, Lane 3: polyadenylation reaction with 1 mM ATP for 30 min, Lane 4: like 3 but 1 mM EATP, Lane 5: like 3 but 0.5 mM EATP and 0.5 mM ATP, Lane 6: like 4 but 16 h incubation, Lane 7: like 5 but 16 h incubation.

Example 4

Figure 8:
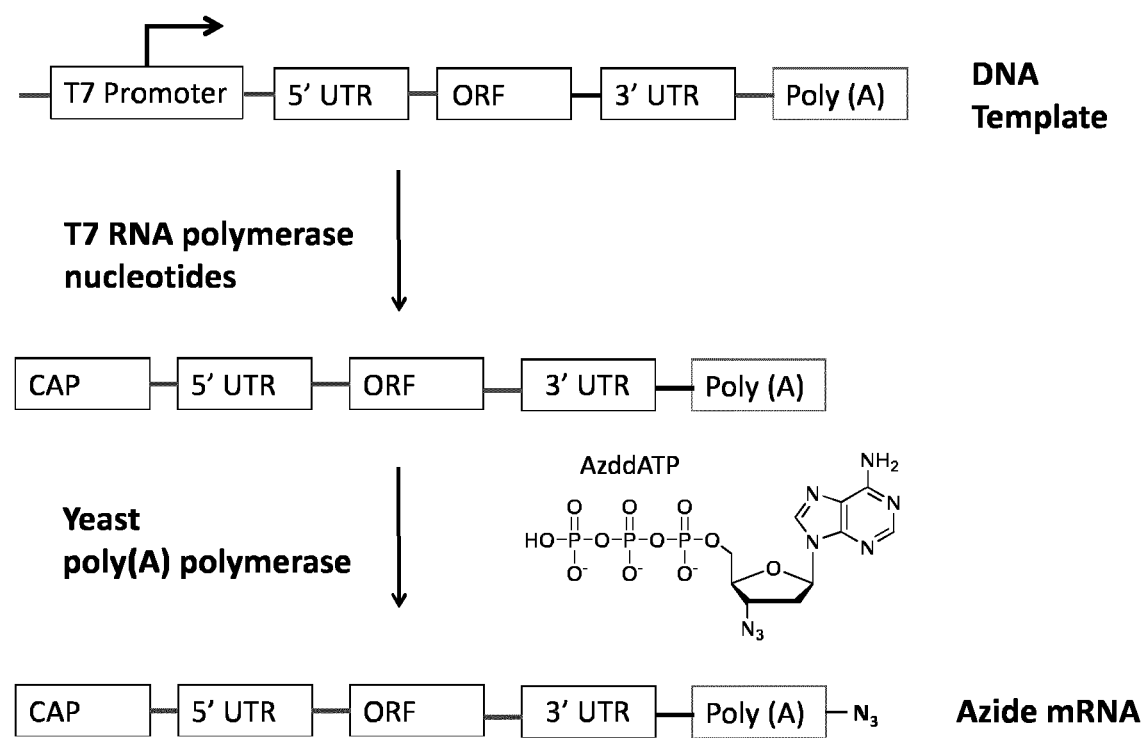
FIG. 8 shows a general scheme of the production of site-specific azide-modified mRNA (single azide at the end of the poly(A) tail only) using yeast poly(A) polymerase and the azide-modified nucleotide AzddATP as described in Example 4.

Azide-modified mRNA coding for the enhanced green fluorescent protein (eGFP) was produced by in vitro transcription (IVT) from a DNA template using T7 RNA polymerase and nucleotide mixture. Here 3'-azido-2',3'-dideoxyadenosine (AzddATP) was incorporated, thus terminating the elongation, in the IVT mRNA after T7 RNA polymerase reaction using yeast poly(A) polymerase to generate a site-specific single azide modified mRNA according to FIG. 8 for subsequent transfection in Henrietta Lacks' immortal cells (HeLa cells). The generated mRNA contains a 5'-cap, untranslated regions (UTR). The protein coding part (open reading frame, ORF) and a poly(A)-tail with a single terminal azide.

mRNA Production

In a 50 µL reaction volume 20 units of T7 RNA polymerase, 1 µg of template DNA and several nucleotides were combined in transcription buffer (40 mM Tris-HCl, pH 7.9, 6 mM $MgCl_2$, 4 mM spermidine, 10 mM dithiothreitol). Final nucleotide concentrations were:

1.0 mM GTP, 4.0 mM A.R.C.A. (P1-(5'-(3'-O-methyl)-7-methyl-guanosyl) P3-(5'-(guanosyl)) triphosphate, cap analog), 1.25 mM CTP, 1.25 mM UTP, 1.25 mM ψUTP (pseudouridine triphosphate), 1.5 mM ATP.

The mixture was incubated for 2 hours at 37° C. and then 2 units of DNAse I were added and incubated for 15 minutes at 37° C. The mRNA was purified by a spin column method according to manufacturers' instruction for PCR products (PCR purification kit from Qiagen). This yielded 13.7 µg of mRNA which was directly used for yeast poly(A) addition with the azide-containing ATP analog AzddATP.

In a 25 µL reaction volume 600 units of yeast poly(A) polymerase, 5.8 µg of purified IVT mRNA and 0.5 mM AzddATP were combined in reaction buffer (10% (v/v) glycerol, 20 mM Tris-HCl, 0.6 mM $MnCl_2$, 20 µM EDTA, 0.2 mM DTT, 100 µg/mL acetylated BSA, pH 7.0) and the solution was incubated for 20 minutes at 37° C. Modified mRNA was purified by a spin column method according to manufacturers' instruction for PCR products (PCR purification kit from Qiagen). This yielded 4.8 µg of mRNA.

Click labelling was performed using 4.8 µg of RNA and 2 nmol of DBCO-sulfo-Cy3 (Jena Bioscience cat. no. CLK-A140-1), combined in a total reaction volume of 30 µL. The reaction mixture was incubated at room temperature overnight and then cleaned using a spin column method according to manufacturers' instruction for PCR products (PCR purification kit from Qiagen). This yielded 4.0 µg of mRNA.

For transfection of modified mRNA a commercial kit (jetMESSENGER™ from POLYPLUS TRANSFECTION®) was used according to manufacturers' instructions using 0.5 µg of Cy3 labeled mRNA and 25.000 HeLa cells (CLS GMBH) reaching confluency. The cells were incubated at 37° C. for 24 hours before analysis under the fluorescent microscope, GFP filter: (470/22 excitation; 510/42 emission) and Cy3 filter (531/40 excitation; 593/40 emission) were used.

Figure 9:
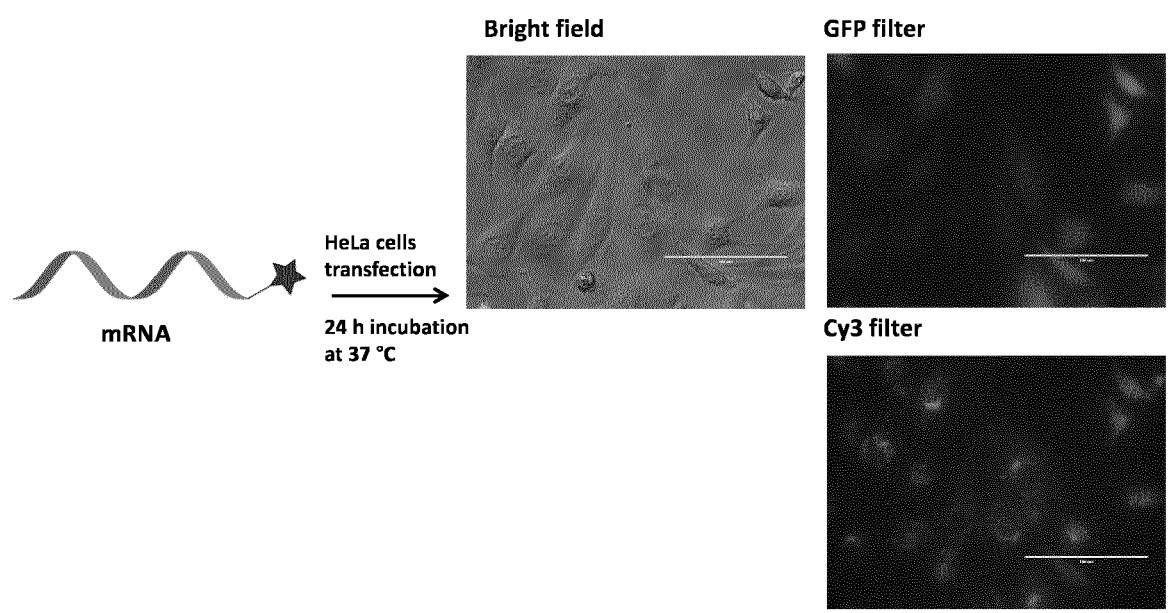
FIG. 9 shows a transfection of 3'-poly(A) tail Cy3 modified mRNA coding for eGFP into HeLa cells. After 24 h incubation at 37° C. green fluorescence of the eGFP was observed (eGFP filter). For the Cy3 labeled mRNA the localization of the mRNA was observed using Cy3 filter settings.
Figure 10:
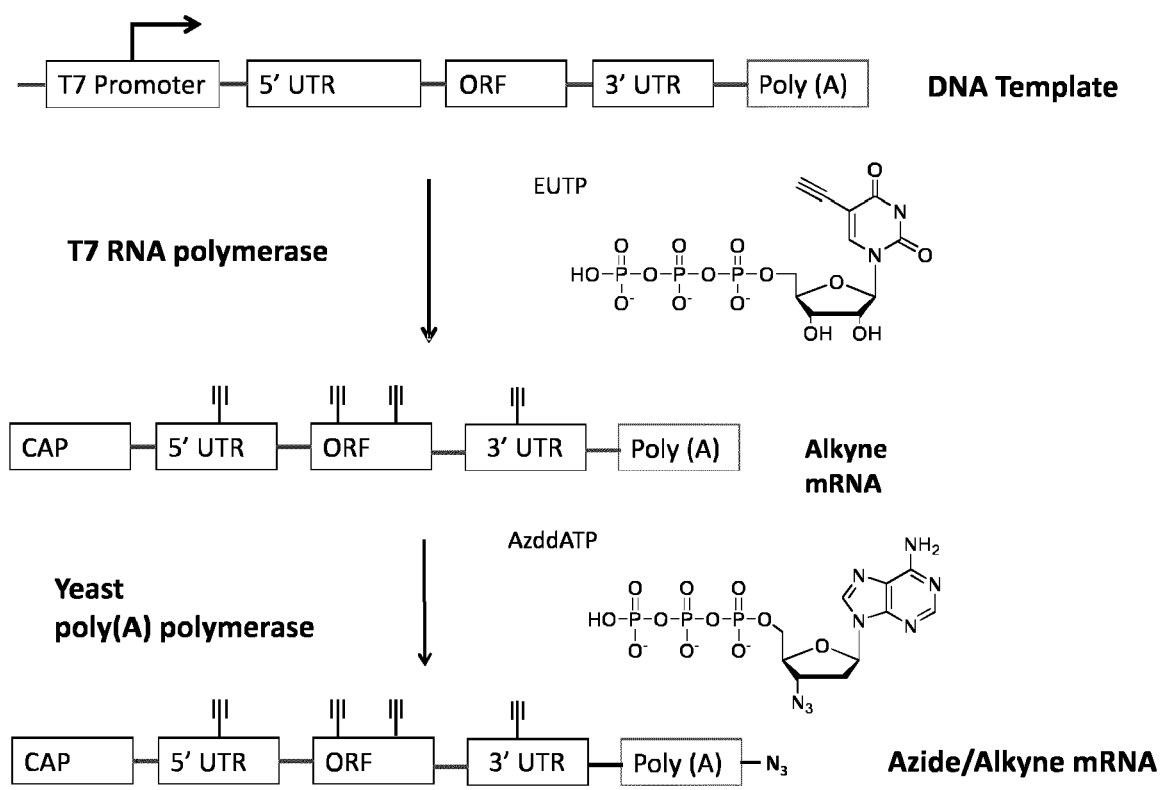
FIG. 10 shows a general scheme for production of double labeled azide/alkyne modified mRNA (internal alkyne groups using T7 RNA polymerase and EUTP, one terminal azide at 3'end using AzddATP and yeast poly(A) polymerase), as in Example 5.

In the bright field image cell morphology of healthy HeLa cells was observed (FIG. 9 shows a), using the GFP filter protein expression of the eGFP was visible (exposure time 120 ms). Localization of the mRNA labelled with Cy3 was observed using the Cy3 filter settings of the microscope.

Example 5

Azide/alkyne-modified mRNA coding for the enhanced green fluorescent protein (eGFP) was produced by in vitro transcription (IVT) from a DNA template using T7 RNA polymerase and nucleotide mixture and yeast poly(A) polymerase. Here 5-ethynyl-uridine-5'-triphosphate (EUTP) was included in the nucleotide mixture to generate an alkyne-modified mRNA followed by incorporation of 3'-azido-2',3'-dideoxyadenosine (AzddATP), thus terminating the elongation and introducing one single azide. This is the first example of dual labelling of the mRNA.

mRNA Production

In a 50 μL reaction volume 20 units of T7 RNA polymerase, 1 μg of template DNA and several nucleotides were combined in transcription buffer (40 mM Tris-HCl, pH 7.9, 6 mM $MgCl_2$, 4 mM spermidine, 10 mM dithiothreitol). Final nucleotide concentrations were:

1.0 mM GTP, 4.0 mM A.R.C.A. (P1-(5'-(3'-O-methyl)-7-methyl-guanosyl) P3-(5'-(guanosyl))triphosphate, Cap Analog), 1.25 mM CTP, 0.625 mM EUTP (5-ethynyluridine triphosphate), 0.625 mM ψUTP (pseudouridine triphosphate), 0.625 mM UTP, 1.5 mM ATP.

The mixture was incubated for 2 hours at 37° C. and then 2 units of DNAse I were added and incubated for 15 minutes at 37° C. The mRNA was purified by a spin column method according to manufacturers' instruction for PCR products (PCR purification kit from Qiagen). This yielded 13.9 μg of mRNA which was directly used for yeast poly(A) addition with the azide-containing ATP analogue AzddATP.

In a 25 μL reaction volume 600 units of Yeast Poly(A) polymerase, 5.8 μg of purified IVT mRNA and 0.5 mM AzddATP were combined in reaction buffer (10% (v/v) glycerol, 20 mM Tris-HCl, 0.6 mM $MnCl_2$, 20 μM EDTA, 0.2 mM DTT, 100 μg/mL acetylated BSA, pH 7.0) and the solution was incubated for 20 minutes at 37° C. Modified mRNA was purified by a spin column method according to manufacturers' instruction for PCR products (PCR purification kit from Qiagen). This yielded 4.35 μg of mRNA.

The first click labelling (strain promoted azide-alkyne cyclo-addition, SPAAC) was performed using 4.35 μg of RNA and 2 nmol of DBCO-sulfo-Cy3 (Jena Bioscience cat no. CLK-A140-1), combined in a total reaction volume of 30 μL. The reaction mixture was incubated at room temperature overnight and then cleaned using a spin column method according to manufacturers' instruction for PCR products (PCR purification kit from Qiagen). This yielded 2.55 μg of mRNA.

A second click reaction (Cu catalysed azide-alkyne Cyclo-addition, CuAAC) was performed with 2 μg of RNA, 1 nmol Eterneon Red 645 Azide (baseclick GmbH), a single reactor pellet and 0.7 μL 10× Activator$^2$ (baseclick GmbH, Oligo$^2$ Click Kit) combined in a total reaction volume of 7 μL. The reaction mixture was incubated at 45° C. for 30 min and then cleaned using a spin column method according to manufacturers' instruction for PCR products (PCR purification kit from Qiagen).

For transfection a commercial kit (jetMESSENGER™ from POLYPLUS TRANSFECTION®) was used according to manufacturers' instructions using 0.5 μg of mRNA and 25,000 HeLa cells (CLS GMBH) reaching confluence. The cells were incubated at 37° C. for 24 hours before analysis under the fluorescent microscope, GFP filter: (470/22Ex; 510/42 Em), Cy5 filter (628/40Ex; 692/40 Em) and Cy3 filter (531/40 excitation; 593/40 emission) were used.

Figure 11:
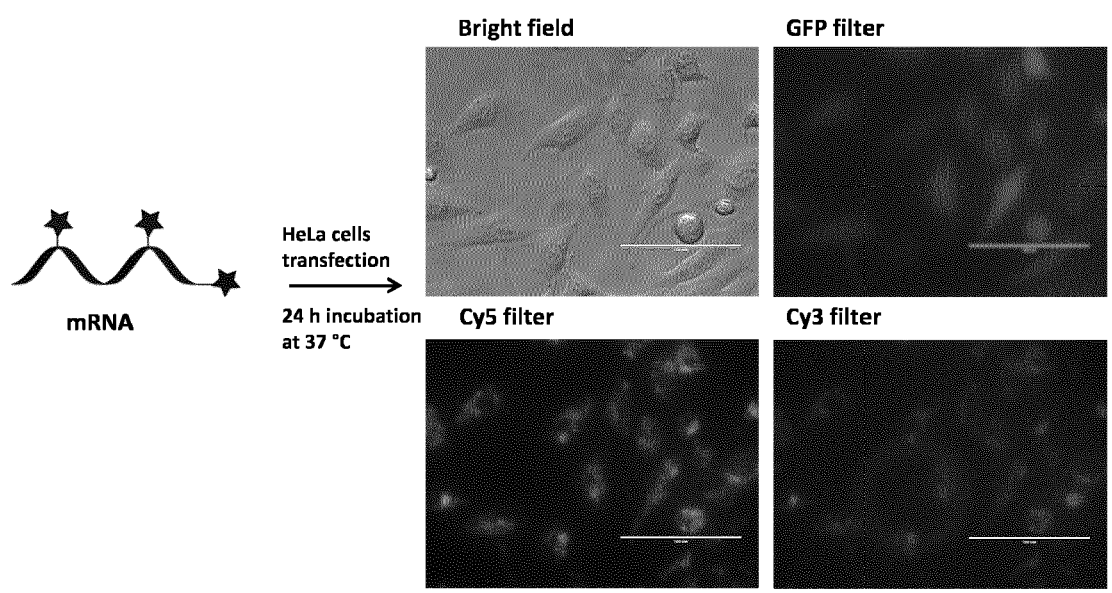
FIG. 11 shows the transfection of internal Eterneon Red modified and 3'-poly(A) tail Cy3 modified mRNA coding for eGFP into HeLa cells. After 24 h incubation at 37° C. green fluorescence of the eGFP was observed (eGFP filter). For the Cy3 labeled mRNA the localization of the mRNA was observed using Cy3 filter settings, for the Eterneon Red labeled mRNA the localization of the mRNA was observed using Cy5 filter settings.

In the bright field image cell morphology of healthy HeLa cells was observed (FIG. 11). Using the GFP filter, protein expression of the eGFP was visible (exposure time 120 ms). Localization of the mRNA labelled with Cy3 and Eterneon Red was observed using the Cy3 and Cy5 filter settings of the microscope, proving dual labelling with two different molecules.

Example 6: Relative Quantification of mRNA Expression Via Fluorescence-Activated Cell Sorting/Scanning (FACS)

This experiment was intended to evaluate the expression level of in vitro transcribed (IVT) eGFP mRNA in cells using a FACS device. eGFP expression is directly monitored via its fluorescence emission at 509 nm upon excitation at 475 nm and can indicate whether introduction of a functional group into the RNA, e.g. a terminal alkyne or a dye molecule can change the expression level. Moreover, uptake of dye-modified mRNA can be monitored on a second fluorescence channel. Variations in the expression level within the cell culture population can be detected to evaluate mRNA preparation homogeneity.

Three different IVT mRNAs were prepared by using the T7 RNA polymerase and a DNA template with different nucleotide mixtures, and if necessary a subsequent click reaction:

A) unmodified nucleotides mixture (=unmodified eGFP mRNA),
B) nucleotide mixture containing 5-ethynyl-uridine 5'-triphosphate (=alkyne modified eGFP mRNA),
C) like B) but subsequent click reaction in the presence of Eterneon-Red azide (Cy5 analog, baseclick GmbH) (=Eterneon Red eGFP mRNA).

2 μg of each mRNA preparation were used for transfection into Henrietta Lacks' immortal cells (HeLa) and buffer without mRNA as a negative control. After 24 h incubation at 37° C. the cells were detached, fixed and then at least 10000 cells were analysed using FACS (FACS Canto II, BECTON DICKINSON).

Figure 12:
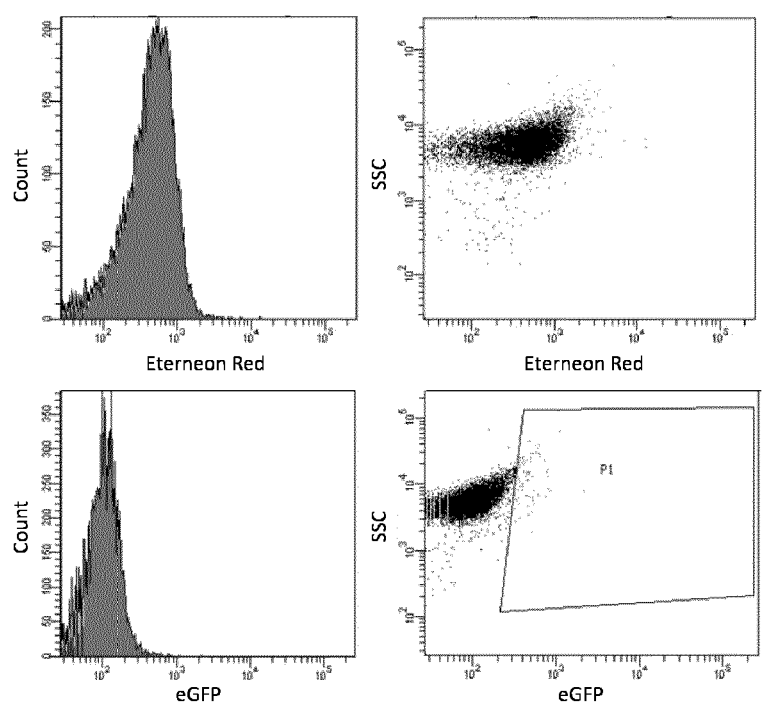
FIGS. 12 to 16 show the results of FACS analyses for untransfected HeLa cells (FIG. 12), HeLa cells transfected with non-modified mRNA encoding eGFP (FIG. 13), HeLa cells transfected with alkyne-modified mRNA encoding eGFP (FIG. 14) and Eterneon Red-/alkyne-modified mRNA encoding eGFP (FIGS. 15 and 16) and allow quantification of protein expression depending on modification and uptake of dye-labeled mRNA (FIGS. 15 and 16).
Figure 13:
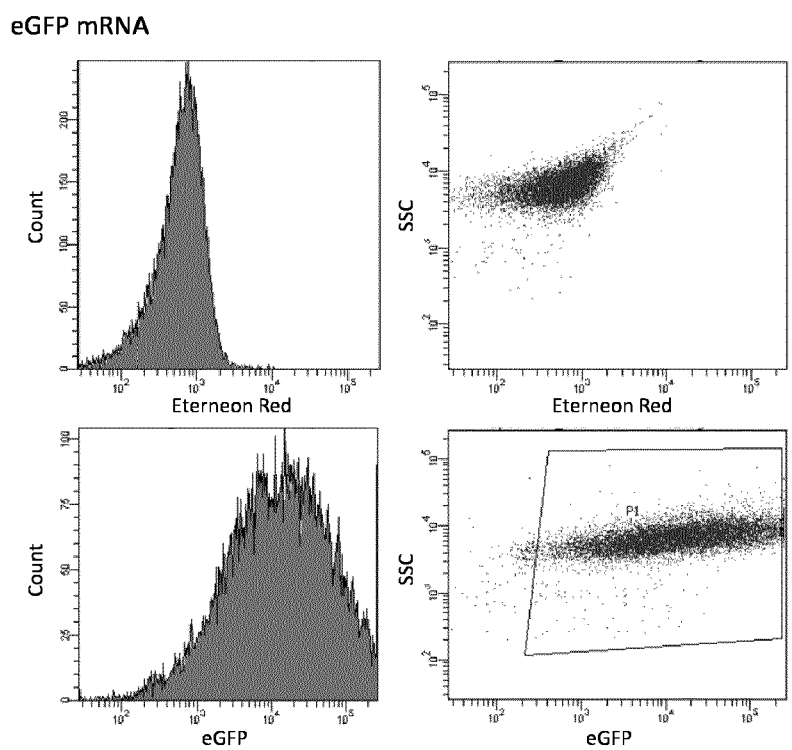
Figure 14:
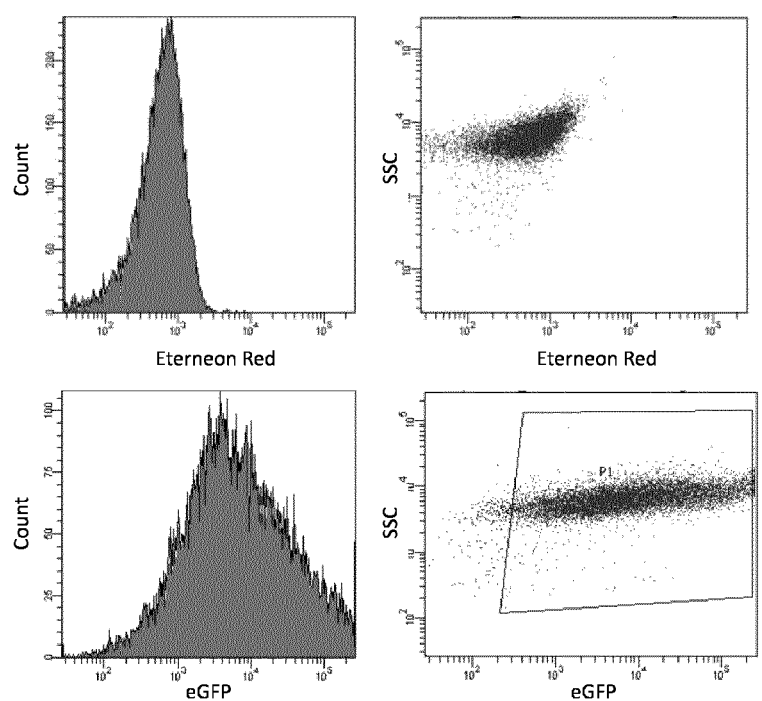
Figure 15:
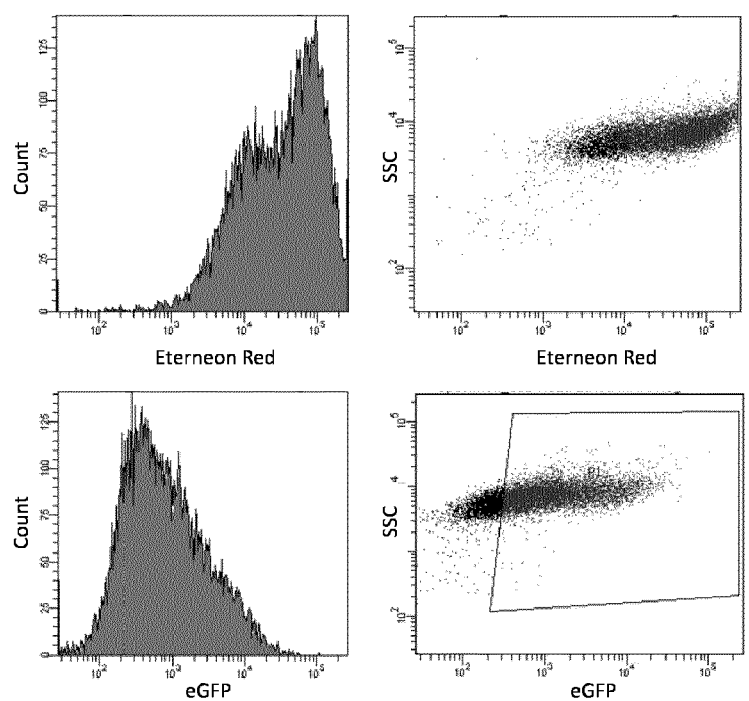
Figure 16:
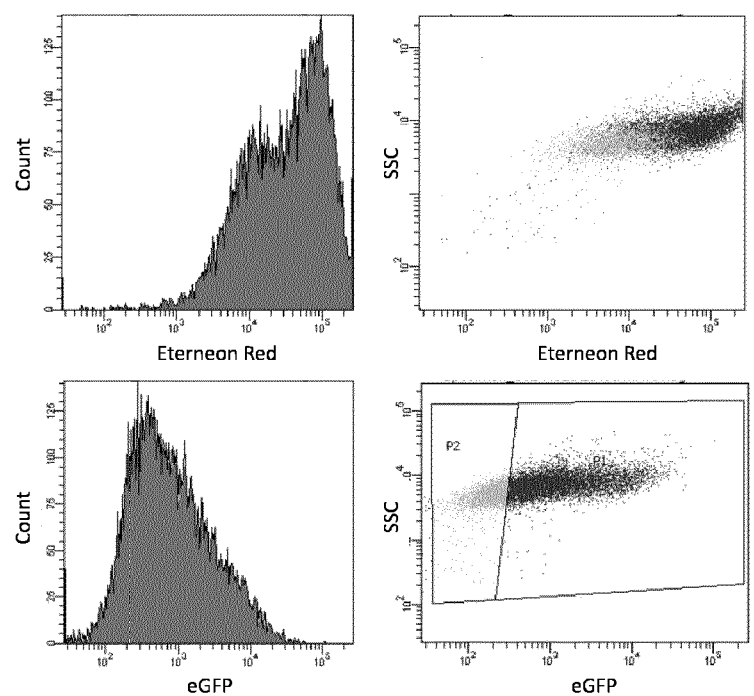
Figure 17:
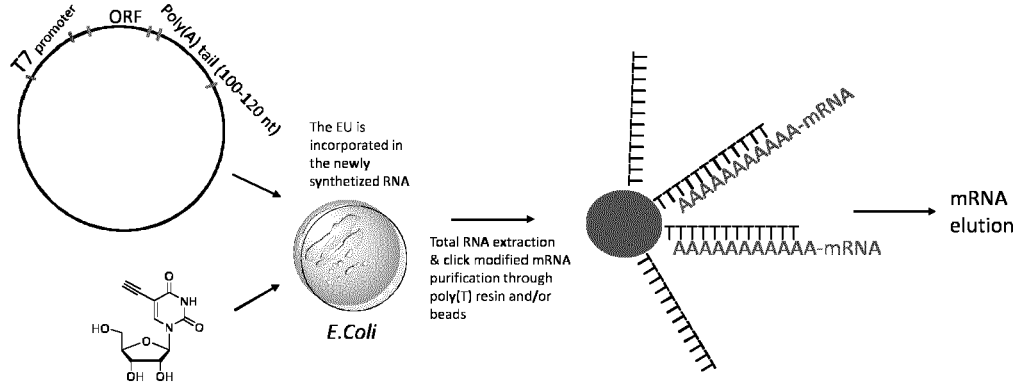
FIG. 17 shows a schematic representation of one embodiment of the invention: Bacterial cells are feeded with, e.g., 5-ethynyluridine and transformed with a plasmid containing the sequence necessary for the production of the mRNA. The newly synthetized mRNA containing EU is then purified by poly(T) resin and/or beads having poly(T) oligonucleotides attached.

All samples were analysed using two channels, one for eGFP fluorescence to evaluate the protein expression and one for the Eterneon Red dye fluorescence to evaluate the presence of dye-labelled mRNA. This resulted in a histogram and dot plot which are shown for each experiment and fluorescence channel as reported below. The histogram displays the number of counted cells per fluorescence intensity and the dot plot displays the cell internal organization (SSC) in correlation to the fluorescence intensity (eGFP or Eterneon Red). Data from 10.000 counts (=10.000 cells) were collected for each sample.

a) HeLa cells, which were not transfected with mRNA, were analysed as a negative control and to establish the level of the intrinsic fluorescence. This allowed to set a gate (P1) in the dot plots which defined the level from which cells are considered expressing the eGFP protein. Every dot inside the P1 gate was defined as an eGFP expressing cell with a specific fluorescence intensity. The result is shown in FIG. 12.
b) When transfected with unmodified eGFP mRNA (A) almost all the cells with P1 equal to 96.5% were expressing the fluorescent protein (red population). The results are shown in FIG. 13. A very similar result was obtained when HeLa cells were transfected with alkyne modified eGFP mRNA (B) and a P1 value of 96.4%. The results of this experiment are shown in FIG. 14.

c) When HeLa cells were transfected with Eterneon Red eGFP mRNA (C) a P1 population of 75% was observed, meaning that even by attaching a sterically demanding dye molecule to the eGFP mRNA the ribosomes are still able to translate it into a functional protein with 78% relative expression level as compared to the unmodified eGFP mRNA. Results can be seen in FIG. 15.

d) Furthermore, because the mRNA was labelled with the Eterneon Red dye it was possible to observe the relative mRNA amount per cell. When the cells defined as not expressing eGFP were analysed (gate P2 in light grey) it was observed that all of them correspond to the cells that did internalize low amounts of Eterneon Red labelled mRNA. This assumption derives from the Eterneon Red channel where P2 (light grey) corresponds to the lowest values of fluorescence intensity. The results are shown in FIG. 16.

with a pharmaceutically acceptable adjuvant or excipient and/or contained in a pharmaceutically acceptable carrier, wherein the modified mRNA contains at least one of an alkyne- or azide modification in at least one nucleotide in
  a) the ORF, the 5'-UTR, and the 3' UTR,
  b) the ORF, the 5'-UTR, the 3'-UTR, and the poly (A) tail region, or
  c) only the poly (A) tail region,
wherein at least one of the following conditions applies:
  (i) the mRNA does not contain a chain-terminating alkyne- or azide-modification at the 3'-ribose position in the poly (A) tail region,
  (ii) at least one of the four standard types of nucleotides is present in modified form compared to the non-modified form in a ratio of 1:4 to 4:1;
  (iii) the modified mRNA contains a functional molecule introduced via a click reaction of the modified mRNA with an alkyne-functional molecule corresponding to an azide modification of the modified mRNA or with an azide-functional molecule corresponding to an alkyne modification of the modified mRNA, which functional molecule is a tissue or cell specific targeting group or ligand, or

---

---

The invention claimed is:

1. A pharmaceutical composition comprising a modified messenger RNA (mRNA) comprising a 5'-cap structure, a 5'-untranslated region (5'-UTR), an open reading frame region (ORF), a 3'-untranslated region (3'-UTR) and a poly (A) tail region as an active agent, optionally in combination (iv) in the ORF and UTRs at least one nucleotide is alkyne-modified and at least one nucleotide is azide-modified.

2. The pharmaceutical composition of claim 1, wherein at least one of the four standard types of nucleotides selected from AMP, CMP, GMP, and UMP in the modified mRNA is partly or completely modified.

3. The pharmaceutical composition of claim 1, characterized in that the modified mRNA contains otherwise modified natural or artificial nucleotides that do not have an alkyne or azide modification.

4. The pharmaceutical composition of claim 1, wherein the modified mRNA contains a detectable label introduced via a click reaction of the modified mRNA with a alkyne-containing detectable label corresponding with an azide modification of the modified mRNA or with an azide-containing label corresponding with an alkyne modification of the mRNA.

5. The pharmaceutical composition of claim 4, wherein the detectable label is a colored or fluorogenic molecule.

6. The pharmaceutical composition of claim 1, wherein the modified mRNA is complexed with a cationic or polycationic compound.

7. The pharmaceutical composition of claim 1, comprising a cell preparation, which is obtained by ex vivo transfection of corresponding human, animal or plant parent cells with the modified mRNA.

8. The pharmaceutical composition of claim 1, wherein the cells are cells of the human or animal immune system.

9. The pharmaceutical composition of claim 1 for use in mRNA based therapeutic and/or prophylactic applications.

10. The pharmaceutical composition for use according to claim 9, wherein the therapeutic and/or prophylactic application comprises targeted delivery in gene replacement therapy, targeted gene therapy in combination with specific endonucleases encoded by the mRNA, in vaccination, in cancer therapy, and for cell specific gene expression or gene editing for treatment of inherited diseases and genetic aberrations, or the use as an immunological adjuvant.

11. A modified messenger RNA (mRNA) comprising a 5'-cap structure, a 5'-untranslated region (5'-UTR), an open reading frame region (ORF), a 3'-untranslated region (3'-UTR) and a poly (A) tail region, characterized in that it contains at least one of an alkyne- or azide modification in at least one nucleotide in
   a) the ORF, the 5'-UTR, and the 3' UTR,
   b) the ORF, the 5'-UTR, the 3'-UTR, and the poly (A) tail region, or
   c) only the poly (A) tail region,
   wherein at least one of the following conditions applies:
   (i) the mRNA does not contain a chain-terminating alkyne- or azide-modification at the 3'-ribose position in the poly (A) tail region,
   (ii) at least one of the four standard types of nucleotides is present in modified form compared to the non-modified form in a ratio of 1:4 to 4:1;
   (iii) the modified mRNA contains a functional molecule introduced via a click reaction of the modified mRNA with an alkyne-functional molecule corresponding to an azide modification of the modified mRNA or with an azide-functional molecule corresponding to an alkyne modification of the modified mRNA, which functional molecule is a tissue or cell specific targeting group or ligand, or
   (iv) in the ORF and UTRs at least one nucleotide is alkyne-modified and at least one nucleotide is azide-modified.

12. The modified mRNA of claim 11, wherein at least one of the four standard types of nucleotides selected from AMP, CMP, GMP, and UMP in the modified mRNA is partly or completely modified.

13. The modified mRNA of claim 11, characterized in that it contains otherwise modified natural or artificial nucleotides that do not have an alkyne or azide modification.

14. The modified mRNA of claim 11, wherein the modified mRNA contains a detectable label introduced via a click reaction of the modified mRNA with an alkyne-containing detectable label corresponding to an azide modification of the modified mRNA or with an azide-containing detectable label corresponding to an alkyne modification of the modified mRNA.

15. The modified mRNA according to claim 14, wherein the detectable label is a colored or fluorogenic molecule.

16. The modified mRNA of claim 11 for use in mRNA based therapeutic and/or prophylactic applications.

17. A kit for production and/or delivery of a modified mRNA of claim 11.

18. A cell preparation, which is obtained by ex vivo transfection of corresponding human, animal or plant cells with a modified mRNA of claim 11.

19. A method for stabilizing mRNA, comprising introducing an alkyne- and/or an azide-modification into said mRNA by including at least one of the four standard types of nucleotides selected from ATP, CTP, GTP and UTP in partly or completely alkyne- and/or azide-modified form during mRNA synthesis and/or in a poly (a) polymerase addition reaction to produce a modified mRNA of claim 11, and optionally one or more of a detectable label and a functional molecule are introduced via a click reaction of the modified mRNA with an alkyne-containing detectable label or functional molecule corresponding to an azide modification of the modified mRNA or with an azide-containing detectable label or functional molecule corresponding to an alkyne modification of the modified mRNA.

20. An in vitro method for quantitatively or qualitatively determining delivery and transfection of a modified mRNA of claim 11 to target cells via fluorescence-activated cell scanning analysis, which modified mRNA contains one or more fluorogenic molecules introduced via a click reaction to the modified mRNA with an alkyne-containing fluorogenic molecule corresponding to an azide modification of the modified mRNA or with an azide-containing fluorogenic molecule corresponding to an alkyne modification of the modified mRNA and/or which modified mRNA encodes a fluorescent protein.

* * * * *